(12) United States Patent
Drmanac

(10) Patent No.: US 7,070,927 B2
(45) Date of Patent: *Jul. 4, 2006

(54) METHODS AND COMPOSITIONS FOR EFFICIENT NUCLEIC ACID SEQUENCING

(75) Inventor: Radoje Drmanac, Palo Alto, CA (US)

(73) Assignee: University of Chicago, Chicago, IL (US)

( * ) Notice: Subject to any disclaimer, the term of this patent is extended or adjusted under 35 U.S.C. 154(b) by 58 days.

This patent is subject to a terminal disclaimer.

(21) Appl. No.: 10/068,301

(22) Filed: Feb. 5, 2002

(65) Prior Publication Data

US 2002/0197621 A1 Dec. 26, 2002

Related U.S. Application Data

(63) Continuation of application No. 09/272,232, filed on Mar. 18, 1999, now Pat. No. 6,401,267, which is a continuation of application No. 08/619,649, filed as application No. PCT/US94/10945 on Sep. 27, 1994, which is a continuation-in-part of application No. 08/303,058, filed on Sep. 8, 1994, now abandoned, which is a continuation-in-part of application No. 08/127,420, filed on Sep. 27, 1993, now abandoned.

(51) Int. Cl.
C12Q 1/68 (2006.01)
G01N 33/53 (2006.01)
C12M 3/00 (2006.01)
C07H 21/04 (2006.01)

(52) U.S. Cl. .................. 435/6; 435/91.1; 435/91.2; 435/7.1; 435/287.1; 536/23.1; 536/24.3; 536/24.32; 536/24.33

(58) Field of Classification Search .............. 435/6, 435/7.1, 91.1, 91.2, 287.1; 536/22.1, 23.1, 536/24.3–24.33
See application file for complete search history.

(56) References Cited

U.S. PATENT DOCUMENTS

| | | | |
|---|---|---|---|
| 4,883,750 A | 11/1989 | Whiteley et al. | 435/6 |
| 4,988,617 A | 1/1991 | Landegren et al. | 435/6 |
| 5,002,867 A | 3/1991 | Macevicz | 435/6 |
| 5,132,418 A | 7/1992 | Caruthers et al. | 536/27 |
| 5,143,854 A | 9/1992 | Pirrung et al. | 436/518 |
| 5,196,305 A | 3/1993 | Findlay et al. | 435/6 |
| 5,202,231 A | 4/1993 | Drmanac et al. | 435/6 |
| 5,242,794 A | 9/1993 | Whiteley et al. | 435/6 |
| 5,348,855 A | 9/1994 | Dattagupta et al. | 435/6 |
| 5,384,261 A | 1/1995 | Winkler et al. | 436/518 |
| 5,424,186 A | 6/1995 | Fodor et al. | 435/6 |
| 5,436,327 A | 7/1995 | Southern et al. | 536/25.34 |
| 5,492,806 A | 2/1996 | Drmanac et al. | 435/5 |
| 5,503,980 A | 4/1996 | Cantor | 435/6 |
| 5,521,065 A | 5/1996 | Whiteley et al. | 435/6 |
| 5,525,464 A | 6/1996 | Drmanac et al. | 435/6 |
| 5,578,832 A | 11/1996 | Trulson et al. | 250/458.1 |
| 5,585,241 A | 12/1996 | Lindmo | 435/6 |
| 5,631,734 A | 5/1997 | Stern et al. | 356/317 |
| 5,695,940 A | 12/1997 | Drmanac et al. | 435/6 |
| 5,744,305 A | 4/1998 | Fodor et al. | 435/6 |
| 5,763,176 A | 6/1998 | Slater et al. | 435/6 |
| 5,800,992 A | 9/1998 | Fodor et al. | 435/6 |
| 5,972,619 A | 10/1999 | Drmanac et al. | 435/6 |
| 6,018,041 A | 1/2000 | Drmanac et al. | 536/24.3 |
| 6,025,136 A | 2/2000 | Drmanac | 435/6 |

FOREIGN PATENT DOCUMENTS

| | | |
|---|---|---|
| WO | WO 89/10977 | 11/1989 |
| WO | WO 90/03382 | 4/1990 |
| WO | WO 90/15070 | 12/1990 |
| WO | WO 91/06678 | 5/1991 |
| WO | WO 93/05183 | 3/1993 |
| WO | WO 95/03401 | 2/1995 |
| WO | WO 95/04160 | 2/1995 |
| WO | WO 95/11995 | 5/1995 |
| WO | WO 95/27078 | 10/1995 |
| WO | WO 96/31622 | 10/1996 |
| WO | WO 97/27325 | 7/1997 |
| WO | WO 97/27327 | 7/1997 |
| WO | WO 97/27331 | 7/1997 |
| WO | WO 99/60170 | 11/1999 |

OTHER PUBLICATIONS

Bains et al., *J. Theor. Biol.*, 135: 303–307 (1988).
Broude et al., *Proc. Natl. Acad. Sci. USA*, 91: 3072–3076 (1994).
Brumbaugh et al., *Proc. Natl. Acad. Sci. USA*, 85: 5610–5614 (1988).
Cantor et al., *Genomics*, 13: 1378–1383 (1992).
Cate et al., *GATA*, 8(3): 102–106 (1991).
Chu et al., *Nucleic Acids Research*, 11(18): 6513–6529 (1983).
Church et al., *Proc. Natl. Acad. Sci. USA*, 81: 1991–1995 (1984).
Church et al., *Science*, 240: 185–188 (1988).
Craig et al., *Nucleic Acids Research*, 17(12): 4605–4610 (1989).
Dahlén et al., *Mol. Cell. Probes*, 1: 159–168 (1987).

(Continued)

*Primary Examiner*—Kenneth R. Horlick
*Assistant Examiner*—Cynthia B. Wilder
(74) *Attorney, Agent, or Firm*—Marshall, Gerstein & Borun LLP

(57) ABSTRACT

Disclosed are novel methods and compositions for rapid and highly efficient nucleic acid sequencing based upon hybridization with two sets of small oligonucleotide probes of known sequences. Extremely large nucleic acid molecules, including chromosomes and non-amplified RNA, may be sequenced without prior cloning or subcloning steps. The methods of the invention also solve various current problems associated with sequencing technology such as, for example, high noise to signal ratios and difficult discrimination, attaching many nucleic acid fragments to a surface, preparing many, longer or more complex probes and labelling more species.

54 Claims, 5 Drawing Sheets

OTHER PUBLICATIONS

Dolinnaya et al., *Nucleic Acids Research*, 16(9): 3721–3738 (1988).
Drmanac et al., *DNA and Cell Biol.*, 9(7): 527–534 (1990).
Drmanac et al., *Electrophoresis*, 13: 566–573 (1992).
Drmanac et al., *Genomics*, 4: 114–128 (1989).
Drmanac et al., *Int. J. Gen. Res.*, 1(1): 59–79 (1992).
Drmanac et al., *J. Biomol. Struct. Dyn.*, 8(5): 1085–1102 (1991).
Drmanac et al., *Science*, 260: 1649–1652 (1993).
Drmanac et al., *Scientia Yugoslavica*, 16(1–2): 97–107 (1990).
Drmanac et al., *The First International Conference on Electrophoresis, Supercomputing and the Human Genome*, Apr. 10–13, 1990, Florida State University, Tallahassee, Florida, C.R. Cantor and H.A. Lim, Eds., World Scientific, Publishers, pp. 47–59.
Drmanac et al., *The Second International Conference on Bioinformatics, Supercomputing and Complex Genome Analysis*, Jun. 4–7, 1992, St. Petersberg Beach, Florida, H.A. Lim, J.W. Fickett, C.R. Cantor, and R.J. Robbins, Eds., World Scientific, Publishers, pp. 121–134 (1993).
Duncan et al., *Analytical Biochemistry*, 169:104–108 (1988).
Eggers et al., *BioTechniques*, 17(3): 516–524 (1994).
Ekins et al., *Trends Biotechnol.*, 17:217–218 (1999).
Fitzgerald et al., *Nucleic Acids Research*, 20(14): 3753–3762 (1992).
Fodor et al., *Clinical Chemistry*, 40(4): 653 (1994).
Fodor et al., *Science*, 251: 767–773 (1991).
Guénoche et al., *Agronomie*, 14: 363–375 (1994).
Hoheisel et al., *FEBS Lett.*, 274(1,2): 103–106 (1990).
Hoheisel et al., *J. Biol. Chem.*, 265(27): 16656–16660 (1990).
Inouye et al., *J. Clin. Microb.*, 28(6): 1469–1472 (1990).
International Search Report; PCT/US94/10945; mailed Feb. 17, 1995.
Ivanov et al., *Nucleic Acids Symp. Ser.*, (24): 189–190 (1991).
Jacobson et al., *Genomics*, 8: 001–007 (1990).
Khorlin et al., *Nucleic Acids Symp Ser.*, (24): 191–192 (1991).
Khrapko et al., *FEBS Lett.*, 256(1,2): 118–122 (1989).
Khrapko et al., *J. DNA Sequencing Mapping*, 1: 375–388 (1991).
Khrapko et al., *Nucleic Acids Research*, 22(3): 364–369 (1994).
Kieleczawa et al., *Science*, 258: 1787–1791 (1992).
Landegren et al., *Science*, 241: 1077–1080 (1988).
Lipshutz et al., *BioTechniques*, 19(3): 442–447 (1995).
Lipshutz et al., *Genomics*, 19: 417–424 (1994).
Lipshutz, *Clinical Chemistry*, 40(6): 1173 (1994).
Lipshutz, *J. Biomol. Struct. Dyn.*, 11(3): 637–653 (1993).
Livshits et al., *J. Biomol. Struct. Dyn.*, 11(4): 783–795 (1994).
Maxam et al., *Proc. Natl. Acad. Sci. USA*, 74(2): 560–564 (1977).
Mirzabekov, *Trend Biotechnol.*, 12:27–32 (1994).
Morrissey et al., *Mol. Cell. Probes*, 3:189–207 (1989).
Murakami et al., *Nucleic Acids Research*, 19(15): 4097–4102 (1997).
Nagata et al., *FEBS Lett.*, 183(2): 379–382 (1985).
Nichols et al., *Nature*, 369: 492–493 (1994).
Pease et al., *Proc. Natl. Acad. Sci. USA*, 91: 5022–5026 (1994).
Pevzner et al., *J. Biomol. Struct. Dyn.*, 7(1):63–73 (1989).
Pevzner et al., *J. Biomol. Struct. Dyn.*, 9(2): 399–410 (1991).
Pontius et al., *Proc. Natl. Acad. Sci. USA*, 88: 8237–8241 (1991).
Postinov et al., *Nucleic Acids Research*, 19(4): 717–725 (1991).
Rasmussen et al., *Analytical Biochemistry*, 198: 138–142 (1991).
Rasmussen, *Nunc. Bulletin*, 10(1) (1992).
Running et al., BioTechniques, 8(3): 276, 279 (1990).
Sanger et al., *Proc. Natl. Acad. Sci. USA*, 74(12): 5463–5467 (1977).
Schriefer et al., *Nucleic Acids Research*, 18(24): 7455 (1990).
Schubert et al., Nucleic Acids Research, 18(11): 3427 (1990).
Shabarova et al., Nucleic Acids Research, 19(15): 4247–4251 (1991).
Sharpe et al., *Food Microbiology*, 6: 261–265 (1989).
Southern et al., *Genomics*, 13: 1008–1017 (1992).
Strezoska et al., Proc. Natl. Acad. Sci. USA, 88: 10089–10093 (1991).
Studier, *Proc. Natl. Acad. Sci. USA*, 86: 6917–6921 (1989).
Szybalski, *Gene*, 90: 177–178 (1990).
Van Ness et al., *Nucleic Acids Research*, 19(12): 3345–3350 (1991).
Wu et al., *Gene*, 76: 245–254 (1989).

METHODS AND COMPOSITIONS FOR EFFICIENT NUCLEIC ACID SEQUENCING

This is a continuation of U.S. application Ser. No. 09/272,232, filed Mar. 18, 1999, (now U.S. Pat. No. 6,401,267, issued Jun. 11, 2002) which in turn is a continuation of U.S. application Ser. No. 08/619,649 filed Mar. 27, 1996, which is a 371 nationalization application of Ser. No. PCT/US94/10945, filed Sep. 27, 1994, which in turn is a continuation-in-part of U.S. application Ser. No. 08/303,058 filed Sep. 8, 1994 (now abandoned), which in turn is a continuation-in-part of U.S. application Ser. No. 08/127,420 filed Sep. 27, 1993 (now abandoned); the entire text and figures of which disclosures are specifically incorporated herein by reference without disclaimer.

The U.S. Government owns rights in the present invention pursuant to Department of Energy grant LDRD 03235 and Contract No. W-31-109-ENG-38 between the U.S. Department of Energy and the University of Chicago, representing Argonne National Laboratory.

BACKGROUND OF THE INVENTION

1. Field of the Invention

The present invention generally relates to the field of molecular biology. The invention particularly provides novel methods and compositions to enable highly efficient sequencing of nucleic acid molecules. The methods of the invention are suitable for sequencing long nucleic acid molecules, including chromosomes and RNA, without cloning or subcloning steps.

2. Description of the Related Art

Nucleic acid sequencing forms an integral part of scientific progress today. Determining the sequence, i.e. the primary structure, of nucleic acid molecules and segments is important in regard to individual projects investigating a range of particular target areas. Information gained from sequencing impacts science, medicine, agriculture and all areas of biotechnology. Nucleic acid sequencing is, of course, vital to the human genome project and other large-scale undertakings, the aim of which is to further our understanding of evolution and the function of organisms and to provide an insight into the causes of various disease states.

The utility of nucleic acid sequencing is evident, for example, the Human Genome Project (HGP), a multinational effort devoted to sequencing the entire human genome, is in progress at various centers. However, progress in this area is generally both slow and costly. Nucleic acid sequencing is usually determined on polyacrylamide gels that separate DNA fragments in the range of 1 to 500 bp, differing in length by one nucleotide. The actual determination of the sequence, i.e., the order of the individual A, G, C and T nucleotides may be achieved in two ways. Firstly, using the Maxam and Gilbert method of chemically degrading the DNA fragment at specific nucleotides (Maxam & Gilbert, 1977), or secondly, using the dideoxy chain termination sequencing method described by Sanger and colleagues (Sanger et al., 1977). Both methods are time-consuming and laborious.

More recently, other methods of nucleic acid sequencing have been proposed that do not employ an electrophoresis step, these methods may be collectively termed Sequencing By Hybridization or SBH (Drmanac et al., 1991; Cantor et al., 1992; Drmanac & Crkvenjakov, U.S. Pat. No. 5,202,231). Development of certain of these methods has given rise to new solid support type sequencing tools known as sequencing chips. The utility of SBH in general is evidenced by the fact that U.S. Patents have been granted on this technology. However, although SBH has the potential for increasing the speed with which nucleic acids can be sequenced, all current SBH methods still suffer from several drawbacks.

SBH can be conducted in two basic ways, often-referred to as Format 1 and Format 2 (Cantor et al., 1992). In Format 1, oligonucleotides of unknown sequence, generally of about 100–1000 nucleotides in length, are arrayed on a solid support or filter so that the unknown samples themselves are immobilized (Strezoska et al., 1991; Drmanac & Crkvenjakov, U.S. Pat. No. 5,202,231). Replicas of the array are then interrogated by hybridization with sets of labeled probes of about 6 to 8 residues in length. In Format 2, a sequencing chip is formed from an array of oligonucleotides with known sequences of about 6 to 8 residues in length (Southern, WO 89/10977; Khrapko et al., 1991; Southern et al., 1992). The nucleic acids of unknown sequence are then labeled and allowed to hybridize to the immobilized oligos.

Unfortunately, both of these SBH formats have several limitations, particularly the requirement for prior DNA cloning steps. In Format 1, other significant problems include attaching the various nucleic acid pieces to be sequenced to the solid surface support or preparing a large set of longer probes. In Format 2, major problems include labelling the nucleic acids of unknown sequence, high noise to signal ratios that generally result, and the fact that only short sequences can be determined. Further problems of Format 2 include the secondary structure formation that prevents access to some targets and the different conditions that are necessary for probes with different GC contents. Therefore, the art would clearly benefit from a new procedure for nucleic acid sequencing, and particularly, one that avoids the tedious processes of cloning and/or subcloning.

SUMMARY OF THE INVENTION

The present invention seeks to overcome these and other drawbacks inherent in the prior art by providing new methods and compositions for the sequencing of nucleic acids. The novel techniques described herein have been generally termed Format 3 by the inventors and represent marked improvements over the existing Format 1 and Format 2 SBH methods. In the Format 3 sequencing provided by the invention, nucleic acid sequences are determined by means of hybridization with two sets of small oligonucleotide probes of known sequences. The methods of the invention allow high discriminatory sequencing of extremely large nucleic acid molecules, including chromosomal material or RNA, without prior cloning, subcloning or amplification. Furthermore, the present methods do not require large numbers of probes, the complex synthesis of longer probes, or the labelling of a complex mixture of nucleic acids segments.

To determine the sequence of a nucleic acid according to the methods of the present invention, one would generally identify sequences from the nucleic acid by hybridizing with complementary sequences from two sets of small oligonucleotide probes (oligos) of defined length and known sequence, which cover most combinations of sequences for that length of probe. One would then analyze the sequences identified to determine stretches of the identified sequences that overlap, and reconstruct or assemble the complete nucleic acid sequence from such overlapping sequences.

The sequencing methods may be conducted using sequential hybridization with complementary sequences from the two sets of small oligos. Alternatively, a mode described as "cycling" may be employed, in which the two sets of small oligos are hybridized with the unknown sequences simultaneously. The term "cycling" is applied as the discriminatory part of the technique comes from then increasing the temperature to "melt" those hybrids that are non-complementary. Such cycling techniques are commonly employed in other areas of molecular biology, such as PCR, and will be readily understood by those of skill in the art in light when reading the present disclosure.

The invention is applicable to sequencing nucleic acid molecules of very long length. As a practical matter, the nucleic acid molecule to be sequenced will generally be fragmented to provide small or intermediate length nucleic acid fragments that may be readily manipulated. The term nucleic acid fragment, as used herein, most generally means a nucleic acid molecule of between about 10 base pairs (bp) and about 100 bp in length. The most preferred methods of the invention are contemplated to be those in which the nucleic acid molecule to be sequenced is treated to provide nucleic acid fragments of intermediate length, i.e., of between about 10 bp and about 40 bp. However, it should be stressed that the present invention is not a method of completely sequencing small nucleic acid fragments, rather it is a method of sequencing nucleic acid molecules per se, which involves determining portions of sequence from within the molecule—whether this is done using the whole molecule, or for simplicity, whether this is achieved by first fragmenting the molecule into smaller sized sections of from about 4 to about 1000 bases.

Sequences from nucleic acid molecules are determined by hybridizing to small oligonucleotide probes of known sequence. In referring to "small oligonucleotide probes", the term "small" means probes of less than 10 bp in length, and preferably, probes of between about 4 bp and about 9 bp in length. In one exemplary sequencing embodiment, probes of about 6 bp in length are contemplated to be particularly useful. For the sets of oligos to cover all combinations of sequences for the length of probe chosen, their number will be represented by $4^F$, wherein F is the length of the probe. For example, for a 4-mer, the set would contain 256 probes; for a 5-mer, the set would contain 1024 probes; for a 6-mer, 4096 probes; a 7-mer, 16384 probes; and the like. The synthesis of oligos of this length is very routine in the art and may be achieved by automated synthesis.

In the methods of the invention, one set of the small oligonucleotide probes of known sequence, which may be termed the first set, will be attached to a solid support, i.e., immobilized on that support in such a way so that they are available to take part in hybridization reactions. The other set of small oligonucleotide probes of known sequence, which may be termed the second set, will be probes that are in solution and that are labelled with a detectable label. The sets of oligos may include probes of the same or different lengths.

The process of sequential hybridization means that nucleic acid molecules, or fragments, of unknown sequence can be hybridized to the distinct sets of oligonucleotide probes of known sequences at separate times (FIG. 1). The nucleic acid molecules or fragments will generally be denatured, allowing hybridization, and added to the first, immobilized set of probes under discriminating hybridization conditions to ensure that only fragments with complementary sequences hybridize. Fragments with non-complementary sequences are removed and the next round of discriminating hybridization is then conducted by adding the second, labelled set of probes, in solution, to the combination of fragments and probes already formed. Labelled probes that hybridize adjacent to a fixed probe will remain attached to the support and can be detected, which is not the case when there is space between the fixed and labelled probes (FIG. 1).

The process of simultaneous hybridization means that the unknown sequence nucleic acid molecules can be contacted with the distinct sets of oligonucleotide probes of known sequences at the same time. Hybridization will occur under discriminating hybridization conditions. Fragments with non-complementary sequences are then "melted", i.e., removed by increasing the temperature, and the next round of discriminating hybridization is then conducted, allowing any complementary second probes to hybridize. Labelled probes that hybridize adjacent to a fixed probe will then be detected in the same manner.

Nucleic acid sequences that are "complementary" are those that are capable of base-pairing according to the standard Watson-Crick complementarity rules, and variations of the rules as they apply to modified bases. That is, that the larger purines, or modified purines, will always base pair with the smaller pyrimidines to form only known combinations. These include the standard paris of guanine paired with Cytosine (G:C) and Adenine paired with either Thymine (A:T), in the case of DNA, or Adenine paired with Uracil (A:U) in the case of RNA. The use of modified bases, or the so-called Universal Base (M, Nichols et al., 1994) is also contemplated.

As used herein, the term "complementary sequences" means nucleic acid sequences that are substantially complementary over their entire length and have very few base mismatches. For example, nucleic acid sequences of six bases in length may be termed complementary when they hybridize at five out of six positions with only a single mismatch. Naturally, nucleic acid sequences that are "completely complementary" will be nucleic acid sequences that are entirely complementary throughout their entire length and have no base mismatches.

After identifying, by hybridization to the oligos of known sequence, various individual sequences that are part of the nucleic acid fragments, these individual sequences are next analyzed to identify stretches of sequences that overlap. For example, portions of sequences in which the 5' end is the same as the 3' end of another sequence, or vice versa, are identified. The complete sequence of the nucleic acid molecule or fragment can then be delineated, i.e., it can be reconstructed from the overlapping sequences thus determined.

The processes of identifying overlapping sequences and reconstructing the complete sequence will generally be achieved by computational analysis. For example, if a labelled probe 5'-TTTTTT-3' hybridizes to the spot containing the fixed probe 5'-AAAAAA-3', a 12-mer sequence from within the nucleic acid molecule is defined, namely 5'-AAAAAATTTTTT-3' (SEQ ID NO:1), i.e. the sequence of the two hybridized probes is combined to reveal a previously unknown sequence. The next question to be answered is which nucleotide follows next after the newly determined 5' AAAAAATTTTTT-3' (SEQ ID NO:1) sequence. There are four possibilities represented by the fixed probe 5'-AAAAAT-3' and labelled probes 5'-TTTTTA-3' for A; 5'-TTTTTT-3' for T; 5'-TTTTTC-3' for C; and 5'-TTTTTG-3' for G. If, for example, the probe 5'-TTTTTC-3' is positive and the other three are negative, then the assembled sequence is extended to 5'-AAAAAATTTTTC-3' (SEQ ID NO:2). In the next step, an algorithm determines which of the labelled probes TTTTCA, TTTTCT, TTTTCC or TTTTCG are positive at the spot containing the fixed probe AAAATT. The process is repeated until all positive (F+P) oligonucleotide sequences are used or defined as false positives.

The present invention thus provides a very effective way to sequence nucleic acid fragments and molecules of long length. Large nucleic acid molecules, as defined herein, are those molecules that need to be fragmented prior to sequencing. They will generally be of at least about 45 or 50 base pairs (bp) in length, and will most often be longer. In fact, the methods of the invention may be used to sequence nucleic acid molecules with virtually no upper limit on length, so that sequences of about 100 bp, 1 kilobase (kb), 100 kb, 1 megabase (Mb), and 50 Mb or more may be sequenced, up to and including complete chromosomes, such as human chromosomes, which are about 100 Mb in length. Such a large number is well within the scope of the present invention and sequencing this number of bases will require two sets of 8-mers or 9-mers (so that F+P≈16–18). The nucleic acids to be sequenced may be DNA, such as cDNA, genomic DNA, microdissected chromosome bands, cosmid DNA or YAC inserts, or may be RNA, including mRNA, rRNA, tRNA or snRNA.

The process of determining the sequence of a long nucleic acid molecule involves simply identifying sequences of length F+P from the molecule and combining the sequences using a suitable algorithm. In practical terms, one would most likely first fragment the nucleic acid molecule to be sequenced to produce smaller fragments, such as intermediate length nucleic acid fragments. One would then identify sequences of length F+P by hybridizing, e.g., sequentially hybridizing, the fragments to complementary sequences from the two sets of small oligonucleotide probes of known sequence, as described above. In this manner, the complete nucleic acid sequence of extremely large molecules can be reconstructed from overlapping sequences of length F+P.

Whether the nucleic acid to be sequenced is itself an intermediate length fragment or is first treated to generate such length fragments, the process of identifying sequences from such nucleic acid fragments by hybridizing to two sets of small oligonucleotide probes of known sequence is central to the sequencing methods disclosed herein. This process generally comprises the following steps:

(a) contacting the set or array of attached or immobilized oligonucleotide probes with the nucleic acid fragments under hybridization conditions effective to allow fragments with a complementary sequence to hybridize sufficiently to a probe, thereby forming primary complexes wherein the fragment has both hybridized and non-hybridized, or "free", sequences;

(b) contacting the primary complexes with the set of labelled oligonucleotide probes in solution under hybridization conditions effective to allow probes with complementary sequences to hybridize to a non-hybridized or free fragment sequence, thereby forming secondary complexes wherein the fragment is hybridized to both an attached (immobilized) probe and a labelled probe;

(c) removing from the secondary complexes any labelled probes that have not hybridized adjacent to an attached probe, thereby leaving only adjacent secondary complexes;

(d) detecting the adjacent secondary complexes by detecting the presence of the label in the labelled probe; and (e) identifying oligonucleotide sequences from the nucleic acid fragments in the adjacent secondary complexes by combining or connecting the known sequences of the hybridized attached and labelled probes.

The hybridization or 'washing conditions' chosen to conduct either one, or both, of the hybridization steps may be manipulated according to the particular sequencing embodiment chosen. For example, both of the hybridization conditions may be designed to allow oligonucleotide probes to hybridize to a given nucleic acid fragment when they contain complementary sequences, i.e., substantially matching sequences, such as those sequences that hybridize at five out of six positions. The hybridization steps would preferably be conducted using a simple robotic device as is routinely used in current sequencing procedures.

Alternatively, the hybridization conditions may be designed to allow only those oligonucleotide probes and fragments that have completely complementary sequences to hybridize. These more discriminating or 'stringent' conditions may be used for both distinct steps of a sequential hybridization process or for either step alone. In such cases, the oligonucleotide probes, whether immobilized or labelled probes, would only be allowed to hybridize to a given nucleic acid fragment when they shared completely complementary sequences with the fragment.

The hybridization conditions chosen will generally dictate the degree of complexity required to analyze the data obtained. Equally, the computer programs available to analyze any data generated may dictate the hybridization conditions that must be employed in a given laboratory. For example, in the most discriminating process, both hybridization steps would be conducted under conditions that allow only oligos and fragments with completely complementary sequences to hybridize. As there will be no mismatched bases, this method involves the least complex computational analyses and, for this reason, it is the currently preferred method for practicing the invention. However, the use of less discriminating conditions for one or both hybridization steps also falls within the scope of the present invention.

Suitable hybridization conditions for use in either or both steps may be routinely determined by optimization procedures or 'pilot studies'. Various types of pilot studies are routinely conducted by those skilled in the art of nucleic acid sequencing in establishing working procedures and in adapting a procedure for use in a given laboratory. For example, conditions such as the temperature; the concentration of each of the components; the length of time of the steps; the buffers used and their pH and ionic strength may be varied and thereby optimized.

In preferred embodiments, the nucleic acid sequencing method of the invention involves a discriminating step to select for secondary hybridization complexes that include immediately adjacent immobilized and labelled probes, as distinct from those that are not immediately adjacent and are separated by one, two or more bases. A variety of processes are available for removing labelled probes that are not hybridized immediately adjacent to an attached probe, i.e., not hybridized back to back, each of which leaves only-the immediately adjacent secondary complexes.

Such discriminatory processes may rely solely on washing steps of controlled stringency wherein the hybridization conditions employed are designed so that immediately adjacently probes remain hybridized due to the increased stability afforded by the stacking interactions of the adjacent nucleotides. Again, washing conditions such as temperature, concentration, time, buffers, pH, ionic strength and the like, may be varied to optimize the removal of labelled probes that are not immediately adjacent.

In preferred embodiments the immediately adjacent immobilized and labelled probes would be ligated, i.e., covalently joined, prior to performing washing steps to remove any non-ligated probes. Ligation may be achieved by treating with a solution containing a chemical ligating agent, such as, e.g., water-soluble carbodiimide or cyanogen bromide. More preferably, a ligase enzyme, such as $T_4$ DNA ligase from $T_4$ bacteriophage, which is commercially available from many sources (e.g., Biolabs), may be employed. In any event, one would then be able to remove non-immediately adjacent labelled probes by more stringent washing conditions that cannot affect the covalently connected labeled and fixed probes.

The remaining adjacent secondary complexes would be detected by observing the location of the label from the labelled probes present within the complexes. The oligonucleotide probes may be labeled with a chemically-detectable label, such as fluorescent dyes, or adequately modified to be detected by a chemiluminescent developing procedure, or radioactive labels such as $^{35}S$, $^{3}H$, $^{32}P$ or $^{33}P$, with $^{33}P$ currently being preferred. Probes may also be labeled with non-radioactive isotopes and detected by mass spectrometry.

Currently, the most preferred method contemplated for practicing the present invention involves performing the hybridization steps under conditions designed to allow only those oligonucleotide probes and fragments that have completely complementary sequences to hybridize and that allow only those probes that are immediately adjacent to remain hybridized. This method subsequently requires the least complex computational analysis.

Where the nucleic acid molecule of unknown sequence is longer than about 45 or 50 bp, one effective method for determining its sequence generally involves treating the molecule to generate nucleic acid fragments of intermediate length, and determining sequences from the fragments. The nucleic acid molecule, whether it be DNA or RNA may be fragmented by any one of a variety of methods including, for example, cutting by restriction enzyme digestion, shearing by physical means such as ultrasound treatment, by NaOH treatment or by low pressure shearing.

In certain embodiments, e.g., involving small oligonucleotide probes between about 4 bp and about 9 bp in length, one may aim to produce nucleic acid fragments of between about 10 bp and about 40 bp in length. Naturally, longer length probes would generally be used in conjunction with sequencing longer length nucleic acid fragment, and vice versa. In certain preferred embodiments, the small oligonucleotide probes used will be about 6 bp in length and the nucleic acid fragments to be sequenced will generally be about 20 bp in length. If desired, fragments may be separated by size to obtain those of an appropriate length, e.g., fragments may be run on a gel, such as an agarose gel, and those with approximately the desired length may be excised.

The method for determining the sequence of a nucleic acid molecule may also be exemplified using the following terms. Initially one would randomly fragment an amount of the nucleic acid to be sequenced to provide a mixture of nucleic acid fragments of length T. One would prepare an array of immobilized oligonucleotide probes of known sequences and length F and a set of labelled oligonucleotide probes in solution of known sequences and length P, wherein $F+P \leq T$ and, preferably, wherein $T \approx 3F$.

One would then contact the array of immobilized oligonucleotide probes with the mixture nucleic acid fragments under hybridization conditions effective to allow the formation of primary complexes with hybridized, complementary sequences of length F and non-hybridized fragment sequences of length T−F. Preferably, the hybridized sequences of length F would contain only completely complementary sequences.

The primary complexes would then be contacted with the set of labelled oligonucleotide probes under hybridization conditions effective to allow the formation of secondary complexes with hybridized, complementary sequences of length F and adjacent hybridized, complementary sequences of length P. In preferred embodiments, only those labelled probes with completely complementary sequences would be allowed to hybridize and only those probes that hybridize immediately adjacent to an immobilized probe would be allowed to remain hybridized. In the most preferred embodiments, the adjacent immobilized and labelled oligonucleotide probes would also be ligated at this stage.

Next one would detect the secondary complexes by detecting the presence of the label and identify sequences of length F+P from the nucleic acid fragments in the secondary complexes by combining the known sequences of the hybridized immobilized and labelled probes. Stretches of the sequences of length F+P that overlap would then be identified, thereby allowing the complete nucleic acid sequence of the molecule to be reconstructed or assembled from the overlapping sequences determined.

In the methods of the invention, the oligonucleotides of the first set may be attached to a solid support, i.e. immobilized, by any of the methods known to those of skill in the art. For example, attachment may be via addressable laser-activated photodeprotection (Fodor et al., 1991; Pease et al., 1994). One generally preferred method is to attach the oligos through the phosphate group using reagents such as nucleoside phosphoramidite or nucleoside hydrogen phosphorate, as described by Southern & Maskos (PCT Patent Application WO 90/03382, incorporated herein by reference), and using glass, nylon or teflon supports. Another preferred method is that of light-generated synthesis described by Pease et al. (1994; incorporated herein by reference). One may also purchase support bound oligonucleotide arrays, for example, as have been offered for sale by Affymetrix and Beckman.

The immobilized oligonucleotides may be formed into an array comprising all probes or subsets of probes of a given length (preferably about 4 to 10 bases), and more preferably, into multiple arrays of immobilized oligonucleotides arranged to form a so-called "sequencing chip". One example of a chip is that where hydrophobic segments are used to create distinct spatial areas. The sequencing chips may be designed for different applications like mapping, partial sequencing, sequencing of targeted regions for diagnostic purposes, mRNA sequencing and large scale genome sequencing. For each application, a specific chip may be designed with different sized probes or with an incomplete set of probes.

In one exemplary embodiment, both sets of oligonucleotide probes would be probes of six bases in length, i.e., 6-mers. In this instance, each set of oligos contains 4096 distinct probes. The first set probes is preferably fixed in an array on a microchip, most conveniently arranged in 64 rows and 64 columns. The second set of 4096 oligos would be labeled with a detectable label and dispensed into a set of distinct tubes. In this example, 4096 of the chips would be combined in a large array, or several arrays. After hybridizing the nucleic acid fragments, a small amount of the labeled oligonucleotides would be added to each microchip for the second hybridization step, only one of each of the 4096 nucleotides would be added to each microchip.

Further embodiments of the invention include kits for use in nucleic acid sequencing. Such kits will generally comprise a solid support having attached an array of oligonucleotide probes of known sequences, as shown in FIG. 2A, FIG. 2B and FIG. 2C, wherein the oligonucleotides are capable of taking part in hybridization reactions, and a set of containers comprising solutions of labelled oligonucleotide probes of known sequences. Arrangements such as those shown in FIG. 4 are also contemplated. This depicts the use of the Universal Base, either as an attachment method, or at the terminus to give an added dimension to the hybridization of fragments.

In the kits, the attached oligonucleotide probes and those in solution may be between about 4 bp and about 9 bp in length, with ones of about 6 bp in length being preferred. The oligos may be labelled with chemically-detectable or radioactive labels, with $^{32}$P-labelled probes being generally preferred, and $^{33}$P-labelled probes being even more preferred. The kits may also comprise a chemical or other ligating agent, such as a DNA ligase enzyme. A variety of other additional compositions and materials may be included in the kits, such as 96-tip or 96-pin devices, buffers, reagents for cutting long nucleic acid molecules and tools for the size selection of DNA fragments. The kits may even include labelled RNA probes so that the probes may be removed by RNAase treatment and the sequencing chips re-used.

BRIEF DESCRIPTION OF THE DRAWINGS

FIG. 2A. Sequencing chips, representing an array of $4^P$ identical sections each containing identical (or different) arrays of oligonucleotides. Sections can be separated by physical barriers or by hydrophobic strips. 4,000–16,000 oligochips are contemplated to be in the array.

FIG. 2B is an enlargement of a chip section containing $4^F$ spots with each with a particular oligonucleotide probe (4,000–16,000) synthesized or spotted on that area. Spots can be as small as several microns and the size of the section is about 1 mm to about 10 mm.

FIG. 2C represents a set of tubes, or one or more multiwell plates, with an appropriate number of wells (in this case $4^P$ wells). Each well contains an amount of a specific labeled oligonucleotide. Additional amounts of the probes can be stored unlabeled if the labeling is not done during synthesis; in this case a sequencing kit will contain necessary components for probe labeling. The lines that are connecting tubes/wells with chip sections depict a step in the sequencing procedure where an amount of a labeled probe is transferred to a chip section. The transferring can be done by pipetting (single or multi-channel) or by pin array transferring liquid by surface tension. Transferring tools can be also included in the sequencing kit.

In FIG. 3A, DNA fragment T1 is such that if contains complete targets for both fixed and non-fixed-labeled probes. FIG. 3B represents the case where the DNA fragment T is not appropriately cut. In FIG. 3C, there is enough space for probe P to hybridize, but the adjacent sequence is not complementary to it. In both case B and case C, the signal will be reduced due to saturation of the molecules of attached probe F. Simultaneous hybridization with DNA fragments and labeled probes and cycling of the hybridization process are some possible ways to increase the yield of correct adjacent hybridizations.

DETAILED DESCRIPTION OF THE PREFERRED EMBODIMENTS

Figure 1A:
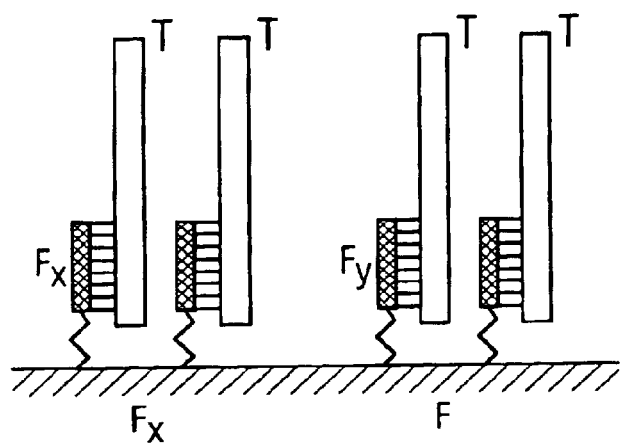
FIG. 1. Basic steps in the hybridization process. Step 1: The unlabelled target DNA to be sequenced (T) is hybridized under discriminative conditions to an array of attached oligonucleotide probes. Spots with probe Fx and Fy are depicted. Complementary sequences for Fx and Fy are at different positions of T. Step 2: Labeled probes, Pi, (one probe per chip) are hybridized to the array. Depicted is a probe that has a complementary target on T that is adjacent to the Fx but not to the Fy. Step 3: By applying discriminative conditions or reagents, complexes with no adjacent probes are selectively melted. A particular example is the ligation of a labelled probe to a fixed probe, when the labelled probe hybridizes "back to back" with the attached probe. Positive signals are detected only in the case of adjacent probes, like Fx and Pi, and in a particular example, only in the case of ligated probes.
Figure 1B:
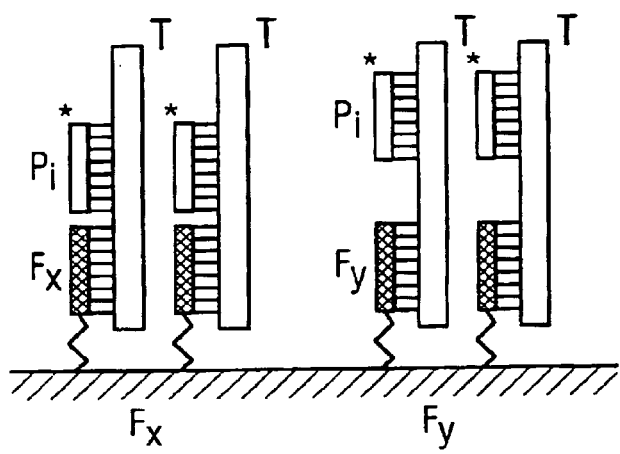
Figure 1C:
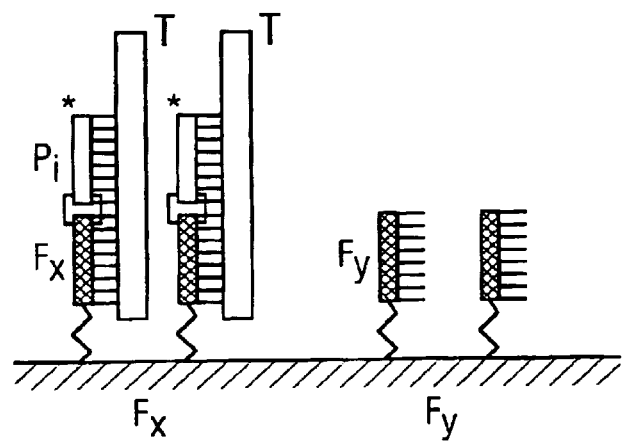

Determining the sequences of nucleic acid molecules is of vital use in all areas of basic and applied biological research (Drmanac & Crkvenjakov, 1990). The present invention provides new and efficient methods for use in sequencing and analyzing nucleic acid molecules. One intended use for this methodology is, in conjunction with other sequencing techniques, for work on the Human Genome Project (HGP).

Presently, two methods of sequencing by hybridization, SBH, are known. In the first, Format 1, unknown genomic DNAs or oligonucleotides of up to about 100–2000 nucleotides in length are arrayed on a solid substrate. These DNAs are then interrogated by hybridization with a set of labeled probes which are generally 6- to 8-mers. In the inverse technique, Format 2, oligomers of 6 to 8 nucleotides are immobilized on a solid support and allowed to anneal to pieces of cloned and labeled DNA.

In either type of SBH analysis, many steps must be included in order to arrive at a definitive sequence. Particular problems of current SBH methods are those associated with the synthesis of large numbers of probes and the difficulties of effective discriminative hybridization. Full match-mismatch discrimination is difficult due to two main reasons. Firstly, the end mismatch of probes longer than 10 bases is very undiscriminative, and secondly, the complex mixture of labeled DNA segments that result when analyzing a long DNA fragment generates a high background.

The present invention provides effective discriminative hybridization without large numbers of probes or probes of increased length, and also eliminates many of the labeling and cloning steps which are particular disadvantages of each of the known SBH methods. The disclosed highly efficient nucleic acid sequencing methods, termed Format 3 sequencing, are based upon hybridization with two sets of small oligonucleotide probes of known sequences, and thus at least double the length of sequence that can be determined. These methods allow extremely large nucleic acid molecules, including chromosomes, to be sequenced and solve various other SBH problems such as, for example, the attachment or labelling of many nucleic acid fragments. The invention is extremely powerful as it may also be used to sequence RNA and even unamplified RNA samples.

Subsequent to the present invention, as disclosed in U.S. Ser. No. 08/127,402 and in Drmanac (1994), another variation of SBH was described termed positional SBH (PSBH) (Broude et al., 1994). PSBH is basically a variant of Format 2 SBH (in which oligonucleotides of known sequences are immobilized and used to hybridize to nucleic acids of unknown sequence that have been previously labelled). In PSBH, the immobilized probes, rather than being simple, single-stranded probes, are duplexes that contain single stranded 3' overhangs. Biotinylated duplex probes are immobilized on streptavidin-coated magnetic beads, to form a type of immobilized probe, and then mixed with $^{32}$P-labeled target nucleic acids to be sequenced. T4 DNA ligase is then added to ligate any hybridized target DNA to the shorter end of the duplex probe.

However, despite representing an interesting approach, PSBH (as reported by Broude et al., 1994) does not reflect a significant advance over the existing SBH technology. For example, unlike the Format 3 methodology of the present invention, PSBH does not extend the length of sequence that can be determined in one round of the method. PSBH also maintains the burdensome requirement for labelling the unknown target DNA, which is not required for Format 3. In general, PSBH is proposed for use in comparative studies or in mapping, rather than in de novo genome sequencing. It thus differs significantly from Format 3 which, although widely applicable to all areas of sequencing, is a very powerful tool for use in sequencing even the largest of genomes.

The nucleic acids to be sequenced may first be fragmented. This may be achieved by any means including, for example, cutting by restriction enzyme digestion, particularly with Cvi JI as described by Fitzgerald et al. (1992); shearing by physical means such as ultrasound treatment; by NaOH treatment, and the like. If desired, fragments of an appropriate length, such as between about 10 bp and about 40 bp may be cut out of a gel. The complete nucleic acid sequence of the original molecule, such as a human chromosome, would be determined by defining F+P sequences present in the original molecule and assembling portions of overlapping F+P sequences. This does not, therefore, require an intermediate step of determining fragment sequences, rather, the sequence of the whole molecule is constructed from F+P sequences delineated.

For the purposes of the following discussion, it will be generally assumed that four bases make up the sequences of the nucleic acids to be sequenced. These are A, G, C and T for DNA and A, G, C and U for RNA. However, it may be advantageous in certain embodiments to use modified bases in the small oligonucleotide probes. To carry out the invention, one would generally first prepare a number of small oligonucleotide probes of defined length that cover all combinations of sequences for that length of probe. This number is represented by $4^N$ (4 to the power N) where the length of the probe is termed N. For example, there are 4096 possible sequences for a 6-mer probe ($4^6$=4096).

One set of such probes of length F ($4^F$) would be fixed in a square array on a microchip—which may be in the range of 1 mm$^2$ or 1 cm$^2$. In the present example, these would be arranged in 64 rows and 64 columns. Naturally, one would ensure that the oligo probes were attached, or otherwise immobilized, to the microchip surface so that were able to take part in hybridization reactions. Another set of oligos of length P, $4^P$ in number, would be also synthesized. The oligos in this "P set" would be labeled with a detectable label and would be dispensed into a set of tubes (FIG. 2A, FIG. 2B and FIG. 2C).

Figure 2A:
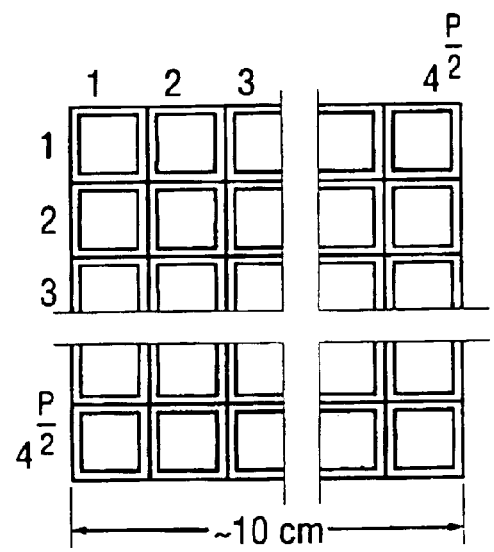
FIG. 2A, FIG. 2B and FIG. 2C represent components of an exemplary sequencing kit.
Figure 2B:
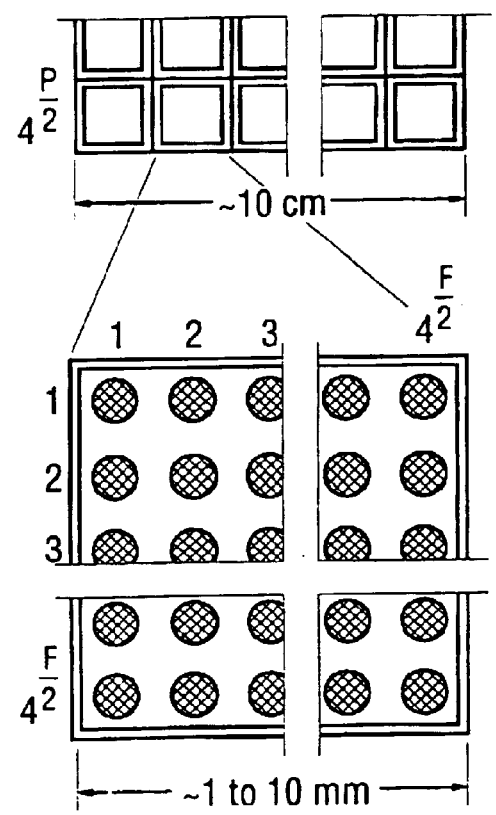
Figure 2C:
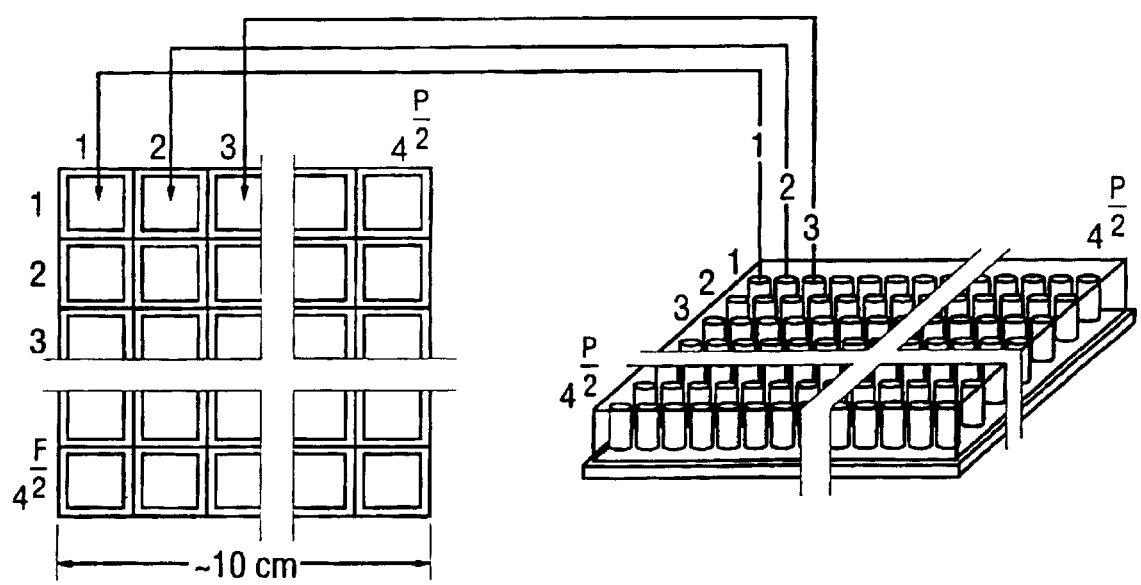

$4^P$ of the chips would be combined in a large array (or several arrays of approximately 10–100 cm$^2$, for a convenient size); where P corresponds to the length of oligonucleotides in the second oligomer set (FIG. 2A, FIG. 2B and FIG. 2C). Again, as a convenient example, P is chosen to be six (P=6).

The nucleic acids to be sequenced would be fragmented to give smaller nucleic acid fragments of unknown sequence. The average length of these fragments, termed T. should generally be greater than the combined length of F and P and may be about three times the length of F (i.e., F+P≦T and T≈3F). In the present example, one would aim to produce nucleic acid fragments of approximately 20 base pairs in length. These fragments would be denatured and added to the large arrays under conditions that facilitate hybridization of complementary sequences.

In the simplest and currently preferred form of the invention, hybridization conditions would be chosen that would allow significant hybridization to occur only if 6 sequential nucleotides in a nucleic acid fragment were complementary to all 6 nucleotides of an F oligonucleotide probe. Such hybridization conditions would be determined by routine optimization pilot studies in which conditions such as the temperature, the concentration of various components, the length of time of the steps, and the buffers used, including the pH of the buffer.

Figure 3A:
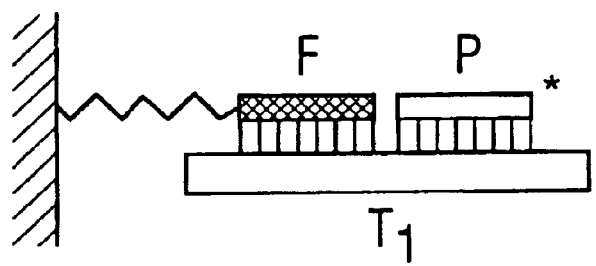
FIG. 3A, FIG. 3B and FIG. 3C. Hybridization of DNA fragments produced by a random cutting of an amount of a DNA molecule.
Figure 3B:
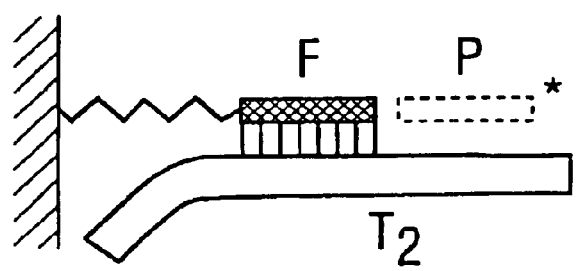
Figure 3C:
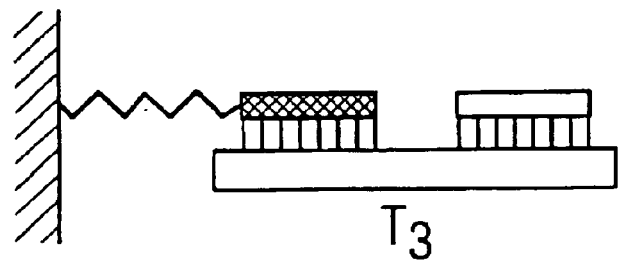

At this stage, each microchip would contain certain hybridized complexes. These would be in the form of probe:fragment complexes in which the entire sequence of the probe is hybridized to the fragment, but in which the fragment, being longer, has some non-hybridized sequences that form a "tail" or "tails" to the complex. In this example, the complementary hybridized sequences would be of length F and the non-hybridized sequences would total T−F in length. The complementary portion of the fragment may be at or towards an appropriate end, so that a single longer non-hybridized tail is formed. Alternatively, the complementary portion of the fragment may be towards the opposite end, so that two non-hybridized tails are formed (FIG. 3A, FIG. 3B and FIG. 3C).

After washing to remove the non-complementary nucleic acid fragments that did not hybridize, a small amount of the labeled oligonucleotides in set P would be added to each microchip for hybridization to the nucleic acid fragment tails of unknown sequence that protrude from the probe:fragment complexes. Only one of each of the $4^P$ nucleotides would be added to each microchip. Again, it is currently preferred to use hybridization conditions that would allow significant binding to occur only if all the 6 nucleotides of a labelled probe were complementary to 6 sequential nucleotides of a nucleic acid fragment tail. The hybridization conditions would be determined by pilot studies, as described above, in which components such as the temperature, concentration, time, buffers and the like, are optimized.

At this stage, each microchip would then contain certain 'secondary hybridized complexes'. These would be in the form of probe:fragment:probe complexes in which the entire sequence of each probe is hybridized to the fragment, and in which the fragment likely has some non-hybridized sequences. In these secondary hybridized complexes the immobilized probe and the labelled probe may be hybridized to the fragment so that the two probes are immediately adjacent or "back to back". However, given that the fragments will generally be longer than the sum of the lengths of the probes, the immobilized probe and the labelled probe may be hybridized to the fragment in non-adjacent positions separated by one or more bases.

The large arrays would then be treated by a process to remove the non-hybridized labelled probes. In preferred embodiments, the process employed would remove not only the non-hybridized labelled probes, but also the non-adjacently-hybridized labelled probes from the array. The process would employ discriminating conditions to allow those secondary hybridization complexes that include adjacent immobilized and labelled probes to be discriminating from those secondary hybridization complexes in which the nucleic acid fragment is hybridized to two probes but which probes are not adjacent. This is an important aspect of the invention in that it will allow the ultimate delineation of a section of fragment sequence corresponding to the combined sequences of the immobilized probe and the labelled probe.

The discrimination process employed to remove non-hybridized and non-adjacently-hybridized probes from the array whilst leaving the adjacently-hybridized probes attached may again be a controlled washing process. The adjacently-hybridized probes would be unaffected by the chosen conditions by virtue of their increased stability due to the stacking reactions of the adjacent nucleotides. However, in preferred embodiments, it is contemplated that one would treat the large arrays so that any adjacent probes would be covalently joined, e.g., by treating with a solution containing a chemical ligating agent or, more preferably, a ligase enzyme, such as $T_4$ DNA ligase (Landegren et al. 1988; Wu & Wallace, 1989).

In any event, the complete array would be subjected to stringent washing so that the only label left associated with the array would be in the form of double-stranded probe-fragment-probe complexes with adjacent hybridized portions of length F+P (i.e., 12 nucleotides in the present example). Using this two step hybridization reaction, very high discrimination is possible because three or four independent discriminative processes are taken into account: discriminative hybridization of fragment T to F bases long probe; discriminative hybridization of P bases long probe to fragment T; discriminative stability of full match (F+T+P) hybrid in comparison to P hybrids or even to mismatched hybrids containing non-adjacent F+P probes; and discriminative ligation of the two end bases of F and P.

One would then detect the so-called adjacent secondary complexes by observing the location of the remaining label on the array. From the position of the label, F+P (e.g., 12) nucleotide long sequences from the fragment could be determined by combining the known sequences of the immobilized and labelled probes. The complete nucleic acid sequence of the original molecule, such as a human chromosome, could then be reconstructed or assembled from the overlapping F+P sequences thus determined.

When ligation is employed in the sequencing process, as is currently preferred, then the ordinary oligonucleotides chip cannot be reused. The inventor contemplates that this will not be limiting as various methods are available for recycling. For example, one may generate a specifically cleavable bond between the probes and then cleave the bond after detection. Alternatively, one may employ ribonucleotides for the second probe, probe P, or use a ribonucleotide for the joining base in probe P, so that this probe may subsequently be removed by RNAase or uracil-DNA glycosylate treatment (Craig et al., 1989). Other contemplated methods are to establish bonds by chemical ligation which can be selectively cut (Dolinnaya et al., 1988).

Further variations and improvements to this sequencing methodology are also contemplated and fall within the scope of the present invention. This includes the use of modified oligonucleotides to increase the specificity or efficiency of the methods, similar to that described by Hoheisel & Lehrach (1990). Cycling hybridizations can also be employed to increase the hybridization signal, as is used in PCR technology. In these cases, one would use cycles with different temperatures to re-hybridize certain probes. The invention also provides for determining shifts in reading frames by using equimolar amounts of probes that have a different base at the end position. For example, using equimolar 7-mers in which the first six bases are the same defined sequence and the last position may be A, T, C or G in the alternative.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) describe the use of biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed CovaLink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/µl) and denaturing for 10 min. at 95° C. and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 µl/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 µl added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (wherein he washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

In more detail, to use this method, a support, such as a glass plate, is derivatized by contact with a mixture of xylene, glycidoxypropyltrimethoxysilane, and a trace of diisopropylethylamine at 90° C. overnight. It is then washed thoroughly with methanol, ether and air-dried. The derivatized support is then heated with stirring in hexaethyleneglycol containing a catalytic amount of concentrated sulfuric acid, overnight in an atmosphere of argon, at 80° C., to yield an alkyl hydroxyl derivatized support. After washing with methanol and ether, the support is dried under vacuum and stored under argon at −20° C.

Oligonucleotide synthesis is then performed by hand under standard conditions using the derivatized glass plate as a solid support. The first nucleotide will be a 3'-hydrogen phosphate, used in the form of the triethylammonium salt. This method results in support bound oligonucleotides of high purity.

An on-chip strategy for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al. (1991); or linked to teflon using the method of Duncan & Cavalier (1988); all references being specifically incorporated herein.

Fodor et al. (1991) describe the light-directed synthesis of dinucleotides which is applicable to the spatially directed synthesis of complex compounds for use in the microfabrication of devices. This is based upon a method that uses light to direct the simultaneous synthesis of chemical compounds on a solid support. The pattern of exposure to light or other forms of energy through a mask, or by other spatially addressable means, determines which regions of the support are activated for chemical coupling. Activation by light results from the removal of photolabile protecting groups from selected areas. After deprotection, a first compound bearing a photolabile protecting group is exposed to the entire surface, but reaction occurs only with regions that were addressed by light in the preceding step. The substrate is then illuminated through a second mask, which activates a different region for reaction with a second protected building block. The pattern of masks used in these illuminations and the sequence of reactants define the ultimate products and their locations. A high degree of miniaturization is possible with the Fodor method because the density of synthesis sites is bounded only by physical limitations on spatial addressability, i.e., the diffraction of light. Each compound is accessible and its position is precisely known. hence, an oligo chip made in this way would be ready for use in SBH.

Fodor et al. (1991) describes the light-activated formation of a dinucleotide as follows. 5'-Nitroveratryl thymidine was synthesized from the 3'-O-thymidine acetate. After deprotection with base, the 5'-nitroveratryl thymidine was attached to an aminated substrate through a linkage to the 3'-hydroxyl group. The nitrovertryl protecting groups were removed by illumination through a 500-µm checkerboard mask. The substrate was then treated with phosphoramidite-activated 2'-deoxycytidine. In order to follow the reaction fluorometrically, the deoxycytidine had been modified with an FMOC-protected aminohexyl linker attached to the exocyclic amine. After removal of the FMOC protecting group with base, the regions that contained the dinucleotide were fluorescently labeled by treatment of the substrate with FITC. Therefore, following this method, support bound-oligonucleotides can be synthesized.

To link an oligonucleotide to a nylon support, as described by Van Ness et al. (1991), requires activation of the nylon surface via alkylation and selective activation of the 5'-amine of oligonucleotides with cyanuric chloride, as follows. A nylon surface is ethylated using triethyloxonium tetrafluoroborate to form amine reactive imidate esters on the surface of the nylon 1-methyl-2-pyrrolidone is used as a solvent. The nylon surface is unpolished to effect the greatest possible surface area.

The activated surface is then reacted with poly (ethyleneimine) ($M_r$~10K–70K) to form a polymer coating that provides an extended amine surface for the attachment of oligos. Amine-tailed oligonucleotide(s) selectively react with excess cyanuric chloride, exclusively on the amine tail, to give a 4,6-dichloro-1,3,5-triazinyl-oligonucleotide(s) in quantitative yield. The displacement of one chlorine moiety of cyanuric chloride by the amino group significantly diminishes the reactivity of the remaining chlorine groups. This results in increased hydrolytic stability of the 4,6-dichloro-1,3,5-triazinyl-oligonucleotide(s) are stable for extended periods in buffered aqueous solutions (pH 8.3, 4° C., 1 week) and are readily isolated and purified by size elusion chromatography or ultrafiltration.

The reaction is specific for the amine tail with no apparent reaction on the nucleotide moieties. The PEI-coated nylon surface is then reacted with the cyanuric chloride activated oligonucleotide. High concentrations of the 'capture' sequence are readily immobilized on the surface and the unreacted amines are capped with succinic anhydride in the final step of the derivatization process.

One particular way to prepare support bound oligonucleotides is to utilize the light-generated synthesis described by Pease et al. (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

Pease et al. (1994) presented a strategy suitable for use in light-directed oligonucleotide synthesis. In this method, the surface of a solid support modified with photolabile protecting groups is illuminated through a photolithographic mask, yielding reactive hydroxyl groups in the illuminated regions. A 3'O-phosphoramidite-activated deoxynucleoside (protected at the 5'-hydroxyl with a photolabile group) is then presented to the surface and coupling occurs at sites that were exposed to light. Following capping, and oxidation, the substrate is rinsed and the surface is illuminated through a second mask, to expose additional hydroxyl groups for coupling. A second 5'-protected, 3' O-phosphoramidite-activated deoxynucleoside is presented to the surface. The selective photodeprotection and coupling cycles are repeated until the desired set of products is obtained. Since photolithography is used, the process can be miniaturized to generate high-density arrays of oligonucleotide probes, the sequence of which is known at each site.

The synthetic pathway for preparing the necessary 5'-O-(α-methyl-6-nitropiperonyloxycabonyl)-N-acyl-2'-deoxynucleoside phosphoramidites (MeNPoc-N-acyl-2'-deoxynucleoside phophoramidites) involves, in the first step, an N-acyl-2'-deoxynucleoside that reacts with 1-(2-nitro-4,5-methylenedioxyphenyl)ethyl-1-chloroformate to yield 5'-MeNPoc-N-acyl-2'-deoxynucleoside. In the second step, the 3'-hydroxyl reacts with 2-cyanoethyl N,N'-diisopropylchlorophosphoramidite, using standard procedures, to yield the 5'-MeNPoc-N-acyl-2'-deoxynucleoside-3'-O-(2-cyanoethyl-N-N-diisopropyl) phosphoramidites. The photoprotecting group is stable under ordinary phosoramidite synthesis conditions and can be removed with aqueous base. These reagents can be stored for long periods under argon at 4° C.

Photolysis half-times of 28 s, 31 s, 27 s, and 18 s for MeNPoc-dT, MeNPoc-dC$^{ib}$, MeNPoc-dG$^{PAC}$, and MeNPoc-dA$^{PAC}$ respectively, have been reported (Pease et al., 1994). In lithographic synthesis, illumination times of 4.5 min (9×t$_{1/2}$MeNPoc-dC) are therefore recommended to ensure >99% removal of MeNPoc protecting groups.

A suitable synthetic support is one consisting of a 5.1×7.6 cm glass substrate prepared by cleaning in concentrated NaOH, followed by exhaustive rinsing in water. The surfaces would then be derivatized for 2 hr with a solution of 10% (vol/vol) bis(2-hydroxyethyl)aminopropyltriethoxysilane (Petrarch Chemicals, Bristol, Pa.) in 95% ethanol, rinsed thoroughly with ethanol and ether, dried in vacuo at 40° C., and heated at 100° C. for 15 min. In such studies, a synthesis linker would be attached by reacting derivatized substrates with 4,4'-dimethoxytrityl (DMT)-hexaethyloxy-O-cyanoethyl phosphoramidite.

In summary, to initiate the synthesis of an oligonucleotide probe, the appropriate deoxynucleoside phosphoramidite derivative would be attached to a synthetic support through a linker. Regions of the support are then activated for synthesis by illumination through, e.g., 800×12800 μm apertures of a photolithographic mask. Additional phosphoramidite synthesis cycles may be performed (with DMT-protected deoxynucleosides) to generate any required sequence, such as any 4-,5-,6-,7-,8-,9- or even 10-mer sequence. Following removal of the phosphate and exocyclic amine protecting groups with concentrated NH$_4$OH for 4 hr, the substrate may then be mounted in a water-jacketed thermostatically controlled hybridization chamber, ready for use.

Of course, one could easily purchase a DNA chip, such as one of the light-activated chips described above, from a commercial source. In this regard, one may contact Affymetrix of Santa Clara, Calif. 95051, and Beckman.

EXAMPLE II

Modified Oligonucleotides for Use in Probes

Modified oligonucleotides may be used throughout the procedures of the present invention to increase the specificity or efficiency of hybridization. A way to achieve this is the substitution of natural nucleotides by base modification. For example, pyrimidines with a halogen at the $C^5$-position may be used. This is believed to improve duplex stability by influencing base stacking. 2,6-diaminopurine may also be used to give a third hydrogen bond in its base pairing with thymine, thereby thermally stabilizing DNA-duplexes. Using 2,6-diaminopurine is reported to lead to a considerable improvement in the duplex stability of short oligomers. Its incorporation is proposed to allow more stringent conditions for primer annealing, thereby improving the specificity of the duplex formation and suppressing background problems or the use of shorter oligomers.

The synthesis of the triphosphate versions of these modified nucleotides is disclosed by Hoheisel & Lehrach (1990, incorporated herein by reference). Briefly, 5-Chloro-2'-deoxyuridine and 2,6-diaminopurine 2'-deoxynucleoside are purchased, e.g., from Sigma. Phosphorylation is carried out as follows: 50 mg dry 2-NH$_2$-dAdo is taken up in 500 μl dry triethyl phosphate stirring under argon. 25 μl POCl$_3$ is added and the mixture incubated at −20° C. In the meantime, 1 mmol pyrophosphoric acid is dissolved in 0.95 ml tri-n-butylamine and 2 ml methanol and dried in a rotary evaporator. Subsequently it is dried by evaporation twice from 5 ml pyridine, with 70 μl tri-n-butylamine also added before the second time. Finally it is dissolved in 2 ml dry dimethyl formamide.

After 90 min at −20° C., the phosphorylation mixture is evaporated to remove excess POCl$_3$ and the tri-n-butylammonium pyrophosphate in dimethyl formamide is added. Incubation is for 1.5 min at room temperature. The reaction is stopped by addition of 5 ml 0.2 M triethylammonium bicarbonate (pH 7.6) and kept on ice for 4 hours. For 5-Cl-dUrd, the conditions would be identical, but 50 μl POCl$_3$ would be added and the phosphorylation carried out at room temperature for 4 hours.

After the hydrolysis, the mixture is evaporated, the pH adjusted to 7.5, and extracted with 1 volume diethyl ether. Separation of the products is, e.g., on a (2.5×20 cm) Q-Sepharose column using a linear gradient of 0.15 M to 0.8 M triethylammonium bicarbonate. Stored frozen, the nucleotides are stable over long periods of time.

One may also use the non-discriminatory base analogue, or universal base, as designed by Nichols et al. (1994). This new analogue, 1-(2'-deoxy-β-D-ribofuranosyl)-3-nitropyrrole (designated M), was generated for use in oligonucleotide probes and primers for solving the design problems that arise as a result of the degeneracy of the genetic code, or when only fragmentary peptide sequence data are available. This analogue maximizes stacking while minimizing hydrogen-bonding interactions without sterically disrupting a DNA duplex.

The M nucleoside analogue was designed to maximize stacking interactions using aprotic polar substituents linked to heteroaromatic rings, enhancing intra- and inter-strand stacking interactions to lessen the role of hydrogen bonding in base-pairing specificity. Nichols et al. (1994) favored 3-nitropyrrole 2'-deoxyribonucleoside because of its structural and electronic resemblance to p-nitroaniline, whose derivatives are among the smallest known intercalators of double-stranded DNA.

The dimethoxytrityl-protected phosphoramidite of nucleoside M is also available for incorporation into nucleotides used as primers for sequencing and polymerase chain reaction (PCR). Nichols et al. (1994) showed that a substantial number of nucleotides can be replaced by M without loss of primer specificity.

A unique property of M is its ability to replace long strings of contiguous nucleosides and still yield functional sequencing primers. Sequences with three, six and nine M substitutions have all been reported to give readable sequencing ladders, and PCR with three different M-containing primers all resulted in amplification of the correct product (Nichols et al., 1994).

The ability of 3-nitropyrrole-containing oligonucleotides to function as primers strongly suggests that a duplex structure must form with complementary strands. Optical thermal profiles obtained for the oligonucleotide pairs d(5'-$C_2$-$T_5$X$T_5$$G_2$-3') and d(5'-$C_2$$A_5$Y$A_5$$G_2$-3') (where X and Y can be A, C, G, T or M) were reported to fit the normal sigmoidal pattern observed for the DNA double-to-single strand transition. The $T_m$ values of the oligonucleotides containing X.M base pairs (where X was A, C, G or T, and Y was M) were reported to all fall within a 3° C. range (Nichols et al., 1994).

EXAMPLE III

Preparation of Sequencing Chips and Arrays

The present example describes physical embodiments of sequencing chips contemplated by the inventor.

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. FIG. 2A, FIG. 2B and FIG. 2C illustrate yet another example of an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45μ pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al. (1989) also used ISO-GRID HGMF from QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the polysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Two basic problems have to be solved. Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 μM/oligonucleotide, Pease et al., 1994) arrayed in 8×12 format (96 chips) with a 1 mM groove in between. Probes are added either by multichannel pipet or pin array, one probe on one chip. To score all 4000 6-mers, 42 chip arrays have to be used, either using different ones, or by reusing one set of chip arrays several times.

Figure 4:
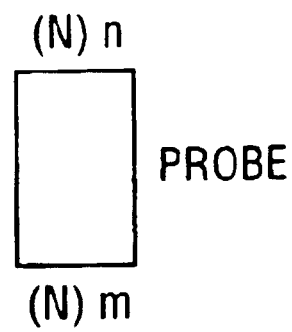
FIG. 4. Use of Universal Base as a linker or in the terminal position for hybridization. The universal bases (M base, Nichols et al., 1994) or all four bases may be added in the probe synthesis. This is a way to increase the length of the probes, and thus stability of the duplexes without increasing the number of probes. Also the use of universal bases at the free end of probes provides a spacer that allow the sequence to be read in a different frame.

In the above case, using the earlier nomenclature of the application, F=9; P=6; and F+P=15. Chips may have probes of formula BxNn, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as (N)nBx(N)m (FIG. 4).

EXAMPLE IV

Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments from the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lacZ minus M13 cloning vector. Sequence analysis of 76 clones showed that CviJI** restricts PyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 μg instead of 2–5 μg); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA, as described in Example VI.

EXAMPLE V

Preparation of Labelled Probes

The oligonucleotide probes may be prepared by automated synthesis, which is routine to those of skill in the art, for example, using an Applied Biosystems system. Alternatively, probes may be prepared using Genosys Biotechnologies Inc. methods using stacks of porous Teflon wafers.

Oligonucleotide probes may be labelled with, for example, radioactive labels ($^{35}S$, $^{32}P$, $^{33}P$, and preferably, $^{33}P$) for arrays with 100–200 μm or 100–400 μm spots; non-radioactive isotopes (Jacobsen et al., 1990); or fluorophores (Brumbaugh et al., 1988). All such labelling methods are routine in the art, as exemplified by the relevant sections in Sambrook et al. (1989) and by further references such as Schubert et al. (1990), Murakami et al. (1991) and Cate et al. (1991), all articles being specifically incorporated herein by reference.

In regard to radiolabeling, the common methods are end-labelling using T4 polynucleotide kinase or high specific activity labelling using Klenow or even T7 polymerase. These are described as follows.

Synthetic oligonucleotides are synthesized without a phosphate group at their 5' termini and are therefore easily labeled by transfer of the $\gamma$-$^{32}P$ or $\gamma$-$^{33}P$ from [$\gamma$-$^{32}P$]ATP or [$\gamma$-$^{33}P$]ATP using the enzyme bacteriophage T4 polynucleotide kinase. If the reaction is carried out efficiently, the specific activity of such probes can be as high as the specific activity of the [$\gamma$-$^{32}P$]ATP or [$\gamma$-$^{33}P$]ATP itself. The reaction described below is designed to label 10 pmoles of an oligonucleotide to high specific activity. Labeling of different amounts of oligonucleotide can easily be achieved by increasing or decreasing the size of the reaction, keeping the concentrations of all components constant.

A reaction mixture would be created using 1.0 μl of oligonucleotide (10 pmoles/μl); 2.0 μl of 10×bacteriophage T4 polynucleotide kinase buffer; 5.0 μl of [$\gamma$-$^{32}P$]ATP or [$\gamma$-$^{33}P$]ATP (sp. act. 5000 Ci/mmole; 10 mCi/ml in aqueous solution) (10 pmoles); and 11.4 μl of water. Eight (8) units (~1 μl) of bacteriophage T4 polynucleotide kinase is added to the reaction mixture mixed well, and incubated for 45 minutes at 37° C. The reaction is heated for 10 minutes at 68° C. to inactivate the bacteriophage T4 polynucleotide kinase.

The efficiency of transfer of $^{32}P$ or $^{33}P$ to the oligonucleotide and its specific activity is then determined. If the specific activity of the probe is acceptable, it is purified. If the specific activity is too low, an additional 8 units of enzyme is added and incubated for a further 30 minutes at 37° C. before heating the reaction for 10 minutes at 68° C. to inactivate the enzyme.

Purification of radiolabeled oligonucleotides can be achieved by precipitation with ethanol; precipitation with cetylpyridinium bromide; by chromatography through biogel P-60; or by chromatography on a Sep-Pak $C_{18}$ column.

Probes of higher specific activities can be obtained using the Klenow fragment of E. coli. DNA polymerase I to synthesize a strand of DNA complementary to the synthetic oligonucleotide. A short primer is hybridized to an oligonucleotide template whose sequence is the complement of the desired radiolabeled probe. The primer is then extended using the Klenow fragment of E. coli DNA polymerase I to incorporate [$\alpha$-$^{32}P$]dNTPs or [$\alpha$-$^{33}P$]dNTPs in a template-directed manner. After the reaction, the template and product are separated by denaturation followed by electrophoresis through a polyacrylamide gel under denaturing conditions. With this method, it is possible to generate oligonucleotide probes that contain several radioactive atoms per molecule of oligonucleotide, if desired.

To use this method, one would mix in a microfuge tube the calculated amounts of [$\alpha$-$^{32}P$]dNTPs or [$\alpha$-$^{33}P$]dNTPs necessary to achieve the desired specific activity and sufficient to allow complete synthesis of all template strands. The concentration of dNTPs should not be less than 1 µM at any stage during the reaction. Then add to the tube the appropriate amounts of primer and template DNAs, with the primer being in three- to tenfold molar excess over the template.

0.1 volume of 10×Klenow buffer would then be added and mixed well. 2–4 units of the Klenow fragment of E. coli DNA polymerase I would then be added per 5 µl of reaction volume, mixed and incubated for 2–3 hours at 4° C. If desired, the progress of the reaction may be monitored by removing small (0.1-µl) aliquots and measuring the proportion of radioactivity that has become precipitable with 10% trichloroacetic acid (TCA).

The reaction would be diluted with an equal volume of gel-loading buffer, heated to 80° C. for 3 minutes, and then the entire sample loaded on a denaturing polyacrylamide gel. Following electrophoresis, the gel is autoradiographed, allowing the probe to be localized and removed from the gel. Various methods for fluorophobic labelling are also available, as follows. Brumbaugh et al. (1988) describe the synthesis of fluorescently labeled primers. A deoxyuridine analog with a primary amine "linker arm" of 12 atoms attached at C-5 is synthesized. Synthesis of the analog consists of derivatizing 2'-deoxyuridine through organometallic intermediates to give 5'(methyl propenoyl)-2'-deoxyuridine. Reaction with dimethoxytrityl-chloride produces the corresponding 5'-dimethoxytrityl adduct. The methyl ester is hydrolyzed, activated, and reacted with an appropriately monoacylated alkyl diamine. After purification, the resultant linker arm nucleosides are converted to nucleoside analogs suitable for chemical oligonucleotide synthesis.

Oligonucleotides would then be made that include one or two linker arm bases by using modified phosphoridite chemistry. To a solution of 50 nmol of the linker arm oligonucleotide in 25 µl of 500 mM sodium bicarbonate (pH 9.4) is added 20 µl of 300 mM FITC in dimethyl sulfoxide. The mixture is agitated at room temperature for 6 hr. The oligonucleotide is separated from free FITC by elution from a 1×30 cm Sephadex G-25 column with 20 mM ammonium acetate (pH 6), combining fractions in the first UV-absorbing peak.

In general, fluorescent labelling of an oligonucleotide at it's 5'-end initially involved two steps. First, a N-protected aminoalkyl phosphoramidite derivative is added to the 5'-end of an oligonucleotide during automated DNA synthesis. After removal of all protecting groups, the NHS ester of an appropriate fluorescent dye is coupled to the 5'-amino group overnight followed by purification of the labelled oligonucleotide from the excess of dye using reverse phase HPLC or PAGE.

Schubert et al. (1990) described the synthesis of a phosphoramidite that enables oligonucleotides labeled with fluorescein to be produced during automated DNA synthesis. Fluorescein methylester is alkylated with 4-chloro(4,4'-dimethoxytrityl)butanol-1 in the presence of $K_2CO_3$ and KI in DMF for 17 hrs. After removal of the trityl group with 1% TFA in chloroform, the product is phosphitylated by standard procedures with bis(diisopropylamino)methoxyphosphine. Phosphorylation of the above obtained fluoresceine derivative leads an H-phosphonate in reasonable yields. The resulting amidite (0.1 M solution in dry acetonitrile) is used for the automated synthesis of different primers using β-cyanoethyl phosphoramidite chemistry and a DNA synthesizer. Cleavage from the support and deprotection is performed with 25% aqueous ammonia for 36 hrs at room temperature. The crude product is purified by PAGE and the labelled primer is visible as a pale green fluorescent band at 310 nm. Elution and desalting using RP 18 cartridges yields the desired product.

The fluorescent labelling of the 5'-end of a probe in the Schubert method is directly achieved during DNA synthesis in the last coupling cycle. Coupling yields are as high as with the normal phosphoramidites. After deprotection and removal of ammonia by lyophilization using a speed vac or by ethanol precipitation, fluorescent labelled oligonucleotides can be directly used for DNA sequencing in Format 3 SBH.

Murakami et al. also described the preparation of fluorescein-labeled oligonucleotides. This synthesis is based on a polymer-supported phosphoramidite and hydrogen phosphonate method. Ethylenediamine or hexamethylenediamine is used as a tether. They were introduced via a phosphoramidate linkage, which was formed by oxidation of a hydrogen-phosphonate intermediate in $CCl_4$ solution. The modified oligonucleotides are subjected to labeling using a primary amine orienting reagent, FITC, on the beads. The resulting modified oligonucleotide is cleaved from beads and subsequently purified by RPLC.

Cate et al. (1991) describe the use of oligonucleotide probes directly conjugated to alkaline phosphatase in combination with a direct chemiluminescent substrate (AMPPD) to allow probe detection. Alkaline phosphatase may be covalently coupled to a modified base of the oligonucleotide. After hybridization, the oligo would be incubated with AMPDD. The alkaline phosphatase enzyme breaks AMPDD to yield a compound that produces fluorescence without excitation, i.e., a laser is not needed. It is contemplated that a strong signal can be generated using such technology.

Labelled probes could readily be purchased from a variety of commercial sources, including $GEN_SET$, rather than synthesized.

EXAMPLE VI

Removal of Phosphate Groups

Both bacterial alkaline phosphatase (BAP) and calf intestinal alkaline phosphatase (CIP) catalyze the removal of 5'-phosphate residues from DNA and RNA. They are therefore appropriate for removing 5' phosphates from DNA and/or RNA to prevent ligation and inappropriate hybridization. Phosphate removal, as described by Sambrook et al. (1989), would be performed after cutting, or otherwise shearing, the genomic DNA.

BAP is the more active of the two alkaline phosphatases, but it is also far more resistant to heat and detergents. It is therefore difficult to inhibit BAP completely at the end of dephosphorylation reactions. Proteinase K is used to digest CIP, which must be completely removed if subsequent ligations are to work efficiently. An alternative method is to inactivate the CIP by heating to 65° C. for 1 hour (or 75° C. for 10 minutes) in the presence of 5 mM EDTA (pH 8.0) and then to purify the dephosphorylated DNA by extraction with phenol:chloroform.

EXAMPLE VII

Conducting Sequencing by Two Step Hybridization

Following are certain examples to describe the execution of the sequencing methodology contemplated by the inventor. First, the whole chip would be hybridized with mixture of DNA as complex as 100 million of bp (one human chromosome). Guidelines for conducting hybridization can be found in papers such as Drmanac et al. (1990); Khrapko et al. (1991); and Broude et al. (1994). These articles teach the ranges of hybridization temperatures, buffers and washing steps that are appropriate for use in the initial step of Format 3 SBH.

The present inventor particularly contemplates that hybridization is to be carried out for up to several hours in high salt concentrations at a low temperature (−2° C. to 5° C.) because of a relatively low concentration of target DNA that can be provided. For this purpose, SSC buffer is used instead of sodium phosphate buffer (Drmanac et al., 1990), which precipitates at 10° C. Washing does not have to be extensive (a few minutes) because of the second step, and can be completely eliminated when the hybridization cycling is used for the sequencing of highly complex DNA samples. The same buffer is used for hybridization and washing steps to be able to continue with the second hybridization step with labeled probes.

After proper washing using a simple robotic device on each array, e.g., a 8×8 mm array (Example III), one labeled, probe, e.g., a 6-mer, would be added. A 96-tip or 96-pin device would be used, performing this in 42 operations. Again, a range of discriminatory conditions could be employed, as previously described in the scientific literature.

The present inventor particularly contemplates the use of the following conditions. First, after adding labeled probes and incubating for several minutes only (because of the high concentration of added oligonucleotides) at a low temperature (0–5° C.), the temperature is increased to 3–10° C., depending on F+P length, and the washing buffer is added. At this time, the washing buffer used is one compatible with any ligation reaction (e.g., 100 mM salt concentration range). After adding ligase, the temperature is increased again to 15–37° C. to allow fast ligation (less than 30 min) and further discrimination of full match and mismatch hybrids.

The use of cationic detergents is also contemplated for use in Format 3 SBH, as described by Pontius & Berg (1991, incorporated herein by reference). These authors describe the use of two simple cationic detergents, dedecyl- and cetyltrimethylammonium bromide (DTAB and CTAB) in DNA renaturation.

DTAB and CTAB are variants of the quaternary amine tetramethylammonium bromide (TMAB) in which one of the methyl groups is replaced by either a 12-carbon (DTAB) or a 16-carbon (CTAB) alkyl group. TMAB is the bromide salt of the tetramethylammonium ion, a reagent used in nucleic acid renaturation experiments to decrease the G-C-content bias of the melting temperature. DTAB and CTAB are similar in structure to sodium dodecyl sulfate (SDS), with the replacement of the negatively charged sulfate of SDS by a positively charged quaternary amine. While SDS is commonly used in hybridization buffers to reduce non-specific binding and inhibit nucleases, it does not greatly affect the rate of renaturation.

When using a ligation process, the enzyme could be added with the labeled probes or after the proper washing step to reduce the background.

Although not previously proposed for use in any SBH method, ligase technology is well established within the field of molecular biology. For example, Hood and colleagues described a ligase-mediated gene detection technique (Landegren et al., 1988), the methodology of which can be readily adapted for use in Format 3 SBH. Landegren et al. describe an assay for the presence of given DNA sequences based on the ability of two oligonucleotides to anneal immediately adjacent to each other on a complementary target DNA molecule. The two oligonucleotides are then joined covalently by the action of a DNA ligase, provided that the nucleotides at the junction are correctly base-paired. Although not previously contemplated, this situation now arises in Format 3 sequencing. Wu & Wallace also describe the use of bacteriophage T4 DNA ligase to join two adjacent, short synthetic oligonucleotides. Their oligo ligation reactions were carried out in 50 mM Tris HCl pH 7.6, 10 mM $MgCl_2$, 1 mM ATP, 1 mM DTT, and 5% PEG. Ligation reactions were heated to 100° C. for 5–10 min followed by cooling to 0° C. prior to the addition of T4 DNA ligase (1 unit; Bethesda Research Laboratory). Most ligation reactions were carried out at 30° C. and terminated by heating to 100° C. for 5 min.

Final washing appropriate for discriminating detection of hybridized adjacent, or ligated, oligonucleotides of length (F+P), is then performed. This washing step is done in water for several minutes at 40–60° C. to wash out all the non ligated labeled probes, and all other compounds, to maximally reduce background. Because of the covalently bound labeled oligonucleotides, detection is simplified (it does not have time and low temperature constrains).

Depending on the label used, imaging of the chips is done with different apparati. For radioactive labels, phosphor storage screen technology and PhosphorImager as a scanner may be used (Molecular Dynamics, Sunnyvale, Calif.). Chips are put in a cassette and covered by a phosphorous screen. After 1–4 hours of exposure, the screen is scanned and the image file stored at a computer hard disc. For the detection of fluorescent labels, CCD cameras and epifluorescent or confocal microscopy are used. For the chips generated directly on the pixels of a CCD camera, detection can be performed as described by Eggers et al. (1994, incorporated herein by reference).

Charge-coupled device (CCD) detectors serve as active solid supports that quantitatively detect and image the distribution of labeled target molecules in probe-based assays. These devices use the inherent characteristics of microelectronics that accommodate highly parallel assays, ultrasensitive detection, high throughput, integrated data acquisition and computation. Eggers et al. (1994) describe CCDs for use with probe-based assays, such as Format 3 SBH of the present invention, that allow quantitative assessment within seconds due to the high sensitivity and direct coupling employed.

The integrated CCD detection approach enables the detection of molecular binding events on chips. The detector rapidly generates a two-dimensional pattern that uniquely characterizes the sample. In the specific operation of the CCD-based molecular detector, distinct biological probes are immobilized directly on the pixels of a CCD or can be attached to a disposable cover slip placed on the CCD surface. The sample molecules can be labeled with radioisotope, chemiluminescent or fluorescent tags.

Upon exposure of the sample to the CCD-based probe array, photons or radioisotope decay products are emitted at the pixel locations where the sample has bound, in the case of Format 3, to two complementary probes. In turn, electron-hole pairs are generated in the silicon when the charged particles, or radiation from the labeled sample, are incident on the CCD gates. Electrons are then collected beneath adjacent CCD gates and sequentially read out on a display module. The number of photoelectrons generated at each pixel is directly proportional to the number of molecular binding events in such proximity. Consequently, molecular binding can be quantitatively determined (Eggers et al., 1994).

As recently reported, silicon-based CCDs have advantages as solid-state detection and imaging sensors primarily because of the high sensitivity of the devices over a wide wavelength range (from 1 to 10000 Å). Silicon is very responsive to electromagnetic radiation from the visible spectrum to soft X-rays. For visible light, a single photon incident on the CCD gate results in a single electron charge packet beneath the gate. A single soft X-ray beta particle (typically KeV to MeV range) generates thousands to tens of thousands of electrons. In addition to the high sensitivity, the CCDs described by Eggers et al. (1994) offer a wide dynamic range (4 to 5 orders of magnitude) since a detectable charge packet can range from a few to $10^5$ electrons. The detection response is linear over a wide dynamic range.

By placing the imaging array in proximity to the sample, the collection efficiency is improved by a factor of at least 10 over lens-based techniques such as those found in conventional CCD cameras. That is, the sample (emitter) is in near contact with the detector (imaging array), and this eliminates conventional imaging optics such as lenses and mirrors.

When radioisotopes are attached as reporter groups to the target molecules, energetic particles are detected. Several reporter groups that emit particles of varying energies have been successfully utilized with the micro-fabricated detectors, including $^{32}P$, $^{33}P$, $^{35}S$, $^{14}C$ and $^{125}L$. The higher energy particles, such as from $^{32}P$, provide the highest molecular detection sensitivity, whereas the lower energy particles, such as from $^{35}S$, provide better resolution. Hence, the choice of the radioisotope reporter can be tailored as required. Once the particular radioisotope label is selected, the detection performance can be predicted by calculating the signal-to-noise ratio (SNR), as described by Eggers et al. (1994).

An alternative luminescent detection procedure involves the use of fluorescent or chemiluminescent reporter groups attached to the target molecules. The fluorescent labels can be attached covalently or through interaction. Fluorescent dyes, such as ethidium bromide, with intense absorption bands in the near UV (300–350 nm) range and principal emission bands in the visible (500–650 nm) range, are most suited for the CCD devices employed since the quantum efficiency is several orders of magnitude lower at the excitation wavelength than at the fluorescent signal wavelength.

From the perspective of detecting luminescence, the polysilicon CCD gates have the built-in capacity to filter away the contribution of incident light in the UV range, yet are very sensitive to the visible luminescence generated by the fluorescent reporter groups. Such inherently large discrimination against UV excitation enables large SNRs (greater than 100) to be achieved by the CCDs as formulated in the incorporated paper by Eggers et al. (1994).

For probe immobilization on the detector, hybridization matrices may be produced on inexpensive $SiO_2$ wafers, which are subsequently placed on the surface of the CCD following hybridization and drying. This format is economically efficient since the hybridization of the DNA is conducted on inexpensive disposable $SiO_2$ wafers, thus allowing reuse of the more expensive CCD detector. Alternatively, the probes can be immobilized directly on the CCD to create a dedicated probe matrix.

To immobilize probes upon the $SiO_2$ coating, a uniform epoxide layer is linked to the film surface, employing an epoxy-silane reagent and standard $SiO_2$ modification chemistry. Amine-modified oligonucleotide probes are then linked to the $SiO_2$ surface by means of secondary amine formation with the epoxide ring. The resulting linkage provides 17 rotatable bonds of separation between the 3' base of the oligonucleotide and the $SiO_2$ surface. To ensure complete amine deprotonation and to minimize secondary structure formation during coupling, the reaction is performed in 0.1 M KOH and incubated at 37° C. for 6 hours.

In Format 3 SBH in general, signals are scored per each of billion points. It would not be necessary to hybridize all arrays, e.g., 4000 5×5 mm, at a time and the successive use of smaller number of arrays is possible.

Cycling hybridizations are one possible method for increasing the hybridization signal. In one cycle, most of the fixed probes will hybridize with DNA fragments with tail sequences non-complementary for labelled probes. By increasing the temperature, those hybrids will be melted (FIG. 3). In the next cycle, some of them (~0.1%) will hybridize with an appropriate DNA fragment and additional labeled probes will be ligated. In this case, there occurs a discriminative melting of DNA hybrids with mismatches for both probe sets simultaneously.

In the cycle hybridization, all components are added before the cycling starts, at the 37° C. for T4, or a higher temperature for a thermostable ligase. Then the temperature is decreased to 15–37° C. and the chip is incubated for up to 10 minutes, and then the temperature is increased to 37° C. or higher for a few minutes and then again reduced. Cycles can be repeated up to 10 times. In one variant, an optimal higher temperature (10–50° C.) can be used without cycling and longer ligation reaction can be performed (1–3 hours).

The procedure described herein allows complex chip manufacturing using standard synthesis and precise spotting of oligonucleotides because a relatively small number of oligonucleotides are necessary. For example if all 7-mer oligos are synthesized (16384 probes), lists of 256 million 14-mers can be determined.

One important variant of the invented method is to use more than one differently labeled probe per basic array. This can be executed with two purposes in mind; multiplexing to reduce number of separately hybridized arrays; or to determine a list of even longer oligosequences such as 3×6 or 3×7. In this case if two labels are used the specificity of the 3 consecutive oligonucleotides can be almost absolute because positive sites must have enough signals of both labels.

A further and additional variant is to use chips containing BxNy probes with y being from 1 to 4. Those chips allow sequence reading in different frames. This can also be achieved by using appropriate sets of labeled probes or both F and P probes could have some unspecified end positions (i.e., some element of terminal degeneracy). Universal bases may also be employed as part of a linker to join the probes of defined sequence to the solid support. This makes the probe more available to hybridization and makes the construct more stable. If a probe has 5 bases, one may, e.g., use 3 universal bases as a linker (FIG. 4).

EXAMPLE VIII

Analyzing the Data Obtained

Image files are analyzed by an image analysis program, like DOTS program (Drmanac et al., 1993), and scaled and evaluated by statistical functions included, e.g., in SCORES program (Drmanac et al., 1994). From the distribution of the signals an optimal threshold is determined for transforming signal into +/− output.

From the position of the label detected, F+P nucleotide sequences from the fragments would be determined by combining the known sequences of the immobilized and labelled probes corresponding to the labelled positions. The complete nucleic acid sequence or sequence subfragments of the original molecule, such as a human chromosome, would then be assembled from the overlapping F+P sequences determined by computational deduction.

One option is to transform hybridization signals e.g., scores, into +/− output during the sequence assembly process. In this case, assembly will start with a F+P sequence with a very high score, for example F+P sequence AAAAAATTTTTT (SEQ ID NO:1). Scores of all four possible overlapping probes AAAAATTTTTA (SEQ ID NO:3), AAAAATTTTTT (SEQ ID NO:4), AAAAATTTTTC (SEQ ID NO:5) and AAAAATTTTTG (SEQ ID NO:6) and three additional probes that are different at the beginning (TAAAAATTTTTT, SEQ ID NO:7; CAAAAATTTTTT, SEQ ID NO:8; GAAAAATTTTTT, SEQ ID NO:9) are compared and three outcomes defined: (i) only the starting probe and only one of the four overlapping probes have scores that are significantly positive relatively to the other six probes, in this case the AAAAAATTTTTT (SEQ ID NO:1) sequence will be extended for one nucleotides to the right; (ii) no one probe except the starting probe has a significantly positive score, assembly will stop, e.g., the AAAAATTTTT (SEQ ID NO:10) sequence is at the end of the DNA molecule that is sequenced; (iii) more than one significantly positive probe among the overlapped and/or other three probes is found; assembly is stopped because of the error or branching (Drmanac et al., 1989).

The processes of computational deduction would employ computer programs using existing algorithms (see, e.g., Pevzner, 1989; Drmanac et al., 1991; Labat and Drmanac, 1993; each incorporated herein by reference).

If, in addition to F+P, F(space 1)P, F(space 2)P, F(space 3)P or F(space 4)P are determined, algorithms will be used to match all data sets to correct potential errors or to solve the situation where there is a branching problem (see, e.g., Drmanac et al., 1989; Bains et al., 1988; each incorporated herein by reference).

EXAMPLE IX

Re-using Sequencing Chips

When ligation is employed in the sequencing process, then the ordinary oligonucleotides chip cannot be immediately reused. The inventor contemplates that this may be overcome in various ways.

One may employ ribonucleotides for the second probe, probe P, so that this probe may subsequently be removed by RNAase treatment. RNAase treatment may utilize RNAase A an endoribonuclease that specifically attacks single-stranded RNA 3' to pyrimidine residues and cleaves the phosphate linkage to the adjacent nucleotide. The end products are pyrimidine 3' phosphates and oligonucleotides with terminal pyrimidine 3' phosphates. RNAase A works in the absence of cofactors and divalent cations.

To utilize an RNAase, one would generally incubate the chip in any appropriate RNAase-containing buffer, as described by Sambrook et al. (1989; incorporated herein by reference). The use of 30–50 μl of RNAase-containing buffer per 8×8 mm or 9×9 mm array at 37° C. for between 10 and 60 minutes is appropriate. One would then wash with hybridization buffer.

Although not widely applicable, one could also use the uracil base, as described by Craig et al. (1989), incorporated herein by reference, in specific embodiments. Destruction of the ligated probe combination, to yield a re-usable chip, would be achieved by digestion with the E. coli repair enzyme, uraci-DNA glycosylase which removes uracil from DNA.

One could also generate a specifically cleavable bond between the probes and then cleave the bond after detection. For example, this may achieved by chemical ligation as described by Shabarova et al. (1991) and Dolinnaya et al. (1988), both references being specifically incorporated herein by reference.

Shabarova et al. (1991) describe the condensation of oligodeoxyribo nucleotides with cyanogen bromide as a condensing agent. In their one step chemical ligation reaction, the oligonucleotides are heated to 97° C., slowly cooled to 0° C., then 1 μl 10M BrCN in acetonitrile is added.

Dolinnaya et al. (1988) show how to incorporate phosphoramidate and pyrophosphate internucleotide bonds in DNA duplexes. They also use a chemical ligation method for modification of the sugar phosphate backbone of DNA, with a water-soluble carbodiimide (CDI) as a coupling agent. The selective cleavage of a phosphoamide bonds involves contact with 15% $CH_3COOH$ for 5 min at 95° C. The selective cleavage of a pyrophosphate bond involves contact with a pyridine-water mixture (9:1) and freshly distilled $(CF_3CO)_2O$.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references, to the extent that they provide exemplary procedural or other details supplementary to those set forth herein, are specifically incorporated herein by reference.

Bains et al., 1988, J. Theor. Biol., 135:303–307.
Broude et al., 1994, Proc. Natl. Acad. Sci. USA, 91:3072–3076.
Brumbaugh et al., 1988, Proc. Natl. Acad. Sci. U.S.A., is 85:5610–5614.
Cantor et al., 1992, Genomics, 13, 1378.
Cate et al., 1991, GATA, 8(3):102–106.
Chu et al., 1983, Nucleic Acids Res., 11:6513–6529.
Craig et al., 1989, Nucleic Acids Research, 17(12):4605.
Dahlen et al., 1987, Mol. Cell. Probes 1:159–168.
Dolinnaya et al., 1988, Nucleic Acids Research, 16(9): 3721–3738.
Drmanac & Crkvenjakov, 1990, Scientia Yugoslavica, 16, 97.

Drmanac & Crkvenjakov, U.S. Pat. No. 5,202,231.
Drmanac et al., 1989, Genomics, 4:114–128.
Drmanac et al., 1991, J. Biomol. Struct. & Dyn., 8:1085.
Drmanac et al., 1991, In "Electrophoreses, Supercomputers and the Human Genome", pp 47–59, World Scientific Publishing Co., Singapore.
Drmanac et al., 1993, Proceedings of 2nd International Conference on Bioinformatics, Supercomputing, and Complex Genome Analysis, World Scientific Publishing Co., pp. 121–134.
Drmanac, 1994, Abstract Book for Genome Mapping and Sequencing; arranged by Richard Myers, David Porteous and Robert Waterstone, Cold Spring Harbor Laboratories, p.60.
Drmanac et al., 1994, Proceedings of the 3rd International Workshop of Transcribed Sequences, In Press.
Duncan & Cavalier, 1988, Analytical Biochemistry, 169:104–108.
Eggers et al., 1994, BioTechniques, 17(3):516–524.
Fitzgerald et al., 1992, Nucleic Acids Research, 20(14): 3753–62.
Fodor et al., 1991, Science, 251:767–768.
Hoheisel & Lehrach, 1990, FEBS Lett., 274(1,2):103–106.
Inouye & Hondo, 1990, J. Clin. Microb., 28:1469–1472.
Jacobsen et al., 1990, Genomics, 8:001–007.
Keller et al., 1988, Anal. Biochem., 170:441–450.
Keller et al., 1989, Anal. Biochem., 177:27–32.
Khrapko et al., 1991, J. DNA Sequencing Mapping, 1, 375.
Labat and Drmanac, 1993, Proceedings of 2nd International Conference on Bioinformations, Supercomputing, and Complex Genome Analysis, World Scientific Publishing Co., pp. 555–565.
Landegren et al. 1988, Science, 241:1077–1080.
Maxam & Gilbert, 1977, Proc. Natl. Acad. Sci., 74, 560.
Morriey & Collins, 1989, Mol. Cell. Probes 3:189–207.
Murakami et al., 1991, Nucleic Acids Research, 19(15): 4097–4102.
Nagata et al., 1985, FEBS Letters, 183:379–382.
Nichols et al., 1994, Nature, 369:492.
Pease et al., 1994 Proc. Natl. Acad. Sci., 91:5022–5026.
Peterkin et al., 1987, BioTechniques 5(2):132–134.
Peterkin et al., 1989, Food Microbiology 5(2):281–284.
Pontius & Berg, 1991, Proc. Natl. Acad. Sci. U.S.A., 88:8237–8241.
Rasmussen et al., 1991, Analytical Biochemistry, 198:138–142.
Sambrook et al., 1989, Molecular cloning: A laboratory manual. Cold Spring Harbor Laboratory. Cold Spring Harbor, N.Y.
Sanger, et al., 1977, Proc. Natl. Acad. Sci., 74, 5463.
Schriefer et al., 1990, Nucleic Acids Research, 18(24):7455.
Schubert et al., 1990, Nucleic Acids Research, 18(11):3427.
Shabarova et al., 1991, Nucleic Acids Research, 19(15) :4247–4251.
Sharp et al., 1989 Food Microbiology, 6:261–265.
Southern, PCT Patent Application WO 89/10977.
Southern & Maskos, PCT Patent Application WO 90/03382.
Southern et al., 1992, Genomics, 13, 1008.
Strezoska et al., 1991, Proc. Natl. Acad. Sci., 88, 10089.
Van Ness et al., 1991, Nucleic Acids Research, 19(12):3345.
Wu & Wallace, 1989 Gene, 76:245–254.
Zeremski and Crkvenjakow, 1993, DNA Sequence Determination by Hybridization: a Strategy for Efficient Large-Scale Sequencing, Science, 260:1649–1652.

What is claimed is:

1. A method of determining a nucleotide sequence of a target nucleic acid, comprising the steps of:
    (a) contacting a target nucleic acid with a set of immobilized oligonucleotide probe(s) and at least one labeled oligonucleotide probe from a set of labeled oligonucleotide probes under hybridization conditions effective to permit hybridization between: (i) complementary sequences of the target nucleic acid and the immobilized probes and (ii) complementary sequences of the target nucleic acid and the labeled probe(s);
    (b) covalently joining immobilized probe(s) and labeled probe(s) which are adjacently hybridized to the same target nucleic acid molecule;
    (c) detecting the labels of the labeled oligonucleotide probe(s) that are covalently joined to the immobilized probe(s);
    (d) identifying at least one nucleotide sequence in the target nucleic acid by steps comprising connecting the nucleotide sequences of the detected labeled oligonucleotide probe(s) with the nucleotide sequences of their respective joined immobilized oligonucleotide probe(s)
    (e) analyzing the sequences identified in step (d) to determine identified sequences that overlap and
    (f) reconstructing said sequence from overlapping oligonucleotide sequences identified in step (e).

2. A method according to claim 1 wherein the set of immobilized oligonucleotide probes comprises a first set of immobilized oligonucleotide probes and the at least one labeled oligonucleotide probe comprises a first labeled oligonucleotide probe, the method further comprising the step of, between steps a) and b): contacting the target nucleic acid with a second set of immobilized oligonucleotide probe(s) and a second labeled oligonucleotide probe under hybridization conditions effective to permit hybridization between: (i) complementary sequences of the target nucleic acid and the immobilized probes of the second set and (ii) complementary sequences of the target nucleic acid and the second labeled oligonucleotide probe, wherein the first and second labeled oligonucleotide probes comprise different nucleotide sequences and the labels of the first and second labeled oligonucletide probes are the same.

3. The method of claim 1 wherein said labels are detected in situ.

4. The method of claim 1, wherein said covalently joining immobilized probe(s) and labeled probe(s) comprises contacting said probes with a ligating agent.

5. The method of claim 4 wherein said labeled probe(s) are contacted with the target nucleic acid at the same time as said ligating agent.

6. The method of claim 1, wherein after step (b) and before step (c), labeled probes that are not covalently joined to an immobilized probe are removed.

7. The method of claim 1 in which labeled probes that are not covalently joined to an immobilized probe are removed under stringent washing conditions.

8. The method of claim 1 in which a plurality of immobilized probes are immobilized on the same support.

9. The method of claim 1 in which immobilized probes having different nucleotide sequences are immobilized on different supports.

10. The method of claim 1 in which the immobilized oligonucleotide probes comprises a plurality of arrays arranged in the form of a sequencing chip.

11. The method of claim 2 in which a plurality of immobilized probes of the first set are immobilized on a support and/or a plurality of immobilized probes of the second set are immobilized on the same support.

12. The method of claim 11 in which the first and second sets of immobilized probes comprise a sequencing chip.

13. The method of claim 2 in which immobilized probes of the first set having different nucleotide sequences are immobilized on different supports and/or immobilized probes of the second set having different nucleotide sequences are immobilized on different supports.

14. The method of claim 1 in which in step (a), the target nucleic acid is contacted with a set of labeled oligonucleotide probes in a sequential manner, one labeled oligonucleotide probe at a time.

15. The method of claim 14 in which in step (a), labeled oligonucleotide probes of the set which have different nucleotide sequences are labeled with the same label.

16. The method of claim 14 in which in step (a), at least two labeled oligonucleotide probes of the set which have different nucleotide sequences are labeled with different labels.

17. The method of claim 14 in which in step (a), the target nucleic acid is contacted simultaneously with the set of immobilized probes and the labeled oligonucleotide probe.

18. The method of claim 14 in which in step (a), the target nucleic acid is contacted first with the set of immobilized probes to form immobilized probe:target complexes and thereafter with the labeled oligonucleotide probe.

19. The method of claim 1 in which in step (a), the target nucleic acid is contacted simultaneously with at least two labeled oligonucleotide probes of a set of labeled oligonucleotide probes, wherein said at least two labeled oligonucleotide probes are labeled with different, distinguishable labels and have different nucleotide sequences that are identifiable by the properties of their respective labels.

20. The method of claim 19 in which in step (a), the target nucleic acid is contacted simultaneously with the set of immobilized probes and said at least two labeled oligonucleotide probes.

21. The method of claim 19 in which in step (a), the target nucleic acid is contacted first with the set of immobilized probes to form immobilized probe:target complexes and thereafter with said at least two labeled oligonucleotide probes.

22. The method of claim 1 in which in step (a), the target nucleic acid is contacted simultaneously with at least two labeled oligonucleotide probes of a set of labeled oligonucleotide probes, wherein said at least two labeled oligonucleotide probes are labeled with different, distinguishable labels and have different nucleotide sequences that are identifiable by the properties of their respective labels and in step (d) the nucleotide sequences of the immobilized and labeled probes are determined by observing in situ the properties of the labels and their relative positions within an array.

23. The method of claim 22 in which in step (a), the target nucleic acid is contacted simultaneously with the array of immobilized probes and said at least two labeled oligonucleotide probes.

24. The method of claim 22 in which in step (a), the target nucleic acid is contacted first with the array of immobilized probes to form immobilized probe:target complexes and thereafter with said at least two labeled oligonucleotide probes.

25. The method of claim 1, wherein the complete nucleotide sequence of the target nucleic acid is determined.

26. The method of claim 1, wherein the target nucleic acid is mapped.

27. The method of claim 1, wherein the target nucleic acid is partially sequenced.

28. The method of claim 1, wherein the immobilized oligonucleotide probes have a length F and the labeled oligonucleotide probes have a length P, where F and P are each independently between 4 and 9 nucleotides.

29. The method of claim 1 wherein said immobilized oligonucleotide probe(s) and/or said labeled probe(s) additionally comprise a universal base or all four bases at the terminal position thereof.

30. The method of claim 1 wherein the target nucleic acid is fragmented prior to step (a).

31. The method of claim 30 wherein the target nucleic acid is fragmented by restriction enzyme digestion, ultrasound treatment, NaOH treatment or low pressure shearing.

32. The method of claim 30 wherein the target nucleic acid fragments have a length T, the immobilized oligonucleotide probes have a length F and the labeled oligonucleotide probes have a length P, where T is between 10 and 100 nucleotides and F and P are each independently between 4 and 9 nucleotides.

33. The method of claim 32 wherein T is between 10 and 40 nucleotides.

34. The method of claim 32 wherein T is about 20 nucleotides.

35. The method of claim 32 wherein T is about 3 times longer than F.

36. The method of any one of claims 32 through 35 wherein F and P are each 6 nucleotides.

37. The method of claim 1 wherein the adjacently hybridized immobilized and labeled probe(s) are covalently joined to one another by enzymatic ligation.

38. The method of any of claims 1 or 2 wherein the hybridization is carried out in cycles.

39. The method of any one of claims 1 or 2 wherein the hybridization conditions are effective to permit hybridization between target nucleic acids and only those immobilized probes and labeled probes that are perfectly complementary to a portion of the target.

40. The method of any one of claims 1 or 2 wherein the hybridization conditions are effective to permit hybridization between those immobilized probes and labeled probes that are immediately adjacent to each other and hybridize to the same target nucleic acid molecule.

41. The method of any one of claims 1 or 2 wherein the target nucleic acid is a cloned DNA, a chromosomal DNA or a mRNA.

42. The method of any one of claims 1 or 2 wherein the immobilized oligonucleotide probes are immobilized by way of covalent attachment.

43. The method of claim 42 wherein the immobilized probes are immobilized via a phosphodiester linkage.

44. The method of claim 42 wherein the immobilized probes are immobilized via a linker.

45. The method of any one of claims 1 or 2 wherein the immobilized probes are immobilized on glass, polystyrene or teflon.

46. The method of any one of claims 1 or 2 wherein the label is a radioactive isotope, non-radioactive isotope or a moiety that emits light.

47. The method of claim 42 wherein the label is a fluorescent dye.

48. The method of any one of claims 1 or 2 wherein the target nucleic acid, an immobilized probe or a labeled probe comprises a modified base or a universal base.

49. The method of any one of claims 1 or 2 wherein the immobilized probe contains a modification to allow the immobilized probe to be reused after said hybridization.

50. The method of claim 49 wherein the oligonucleotides of the labeled probe comprise ribonucleotides.

51. The method of claim 50 wherein said covalently joined labeled probe comprising ribonucleotides is removed from the immobilized probe by RNAase treatment.

52. The method of claim 49 wherein the covalently joined labeled probe comprises a uracil base.

53. The method of claim 52 wherein said covalently joined labeled probe comprising a uracil base is removed from the immobilized probe by uracil-DNA glycosylase treatment.

54. The method of claim 49 wherein said labeled probe comprises a chemically cleavable bond.

* * * * *

UNITED STATES PATENT AND TRADEMARK OFFICE
CERTIFICATE OF CORRECTION

PATENT NO. : 7,070,927 B2  Page 1 of 1
APPLICATION NO. : 10/068301
DATED : July 4, 2006
INVENTOR(S) : Radoje T. Drmanac It is certified that error appears in the above-identified patent and that said Letters Patent is hereby corrected as shown below:

At Column 35, line 53, "oligonucletide" should be -- oligonucleotide --.

At Column 37, lines 16-17, "nucle- otidle" should be -- nucle- otide --.

Signed and Sealed this

Twentieth Day of March, 2007

JON W. DUDAS
*Director of the United States Patent and Trademark Office*

SEQUENCE LISTING

<160> NUMBER OF SEQ ID NOS: 10

<210> SEQ ID NO 1
<211> LENGTH: 12
<212> TYPE: DNA
<213> ORGANISM: Artificial sequence
<220> FEATURE:
<223> OTHER INFORMATION: Primer

<400> SEQUENCE: 1
aaaaaatttt tt                                                          12

<210> SEQ ID NO 2
<211> LENGTH: 13
<212> TYPE: DNA
<213> ORGANISM: Artificial sequence
<220> FEATURE:
<223> OTHER INFORMATION: Primer

<400> SEQUENCE: 2
aaaaaatttt ttc                                                         13

<210> SEQ ID NO 3
<211> LENGTH: 12
<212> TYPE: DNA
<213> ORGANISM: Artificial sequence
<220> FEATURE:
<223> OTHER INFORMATION: Primer

<400> SEQUENCE: 3

-continued aaaaatttt ta                                                    12

<210> SEQ ID NO 4
<211> LENGTH: 12
<212> TYPE: DNA
<213> ORGANISM: Artificial sequence
<220> FEATURE:
<223> OTHER INFORMATION: Primer

<400> SEQUENCE: 4 aaaaatttt tt                                                    12

<210> SEQ ID NO 5
<211> LENGTH: 12
<212> TYPE: DNA
<213> ORGANISM: Artificial sequence
<220> FEATURE:
<223> OTHER INFORMATION: Primer

<400> SEQUENCE: 5 aaaaatttt tc                                                    12

<210> SEQ ID NO 6
<211> LENGTH: 12
<212> TYPE: DNA
<213> ORGANISM: Artificial sequence
<220> FEATURE:
<223> OTHER INFORMATION: Primer

<400> SEQUENCE: 6 aaaaatttt tg                                                    12

<210> SEQ ID NO 7
<211> LENGTH: 12
<212> TYPE: DNA
<213> ORGANISM: Artificial sequence
<220> FEATURE:
<223> OTHER INFORMATION: Primer

<400> SEQUENCE: 7
taaaaatttt tt                                                   12

<210> SEQ ID NO 8
<211> LENGTH: 12
<212> TYPE: DNA
<213> ORGANISM: Artificial sequence
<220> FEATURE:
<223> OTHER INFORMATION: Primer

<400> SEQUENCE: 8
caaaaatttt tt                                                   12

<210> SEQ ID NO 9
<211> LENGTH: 12
<212> TYPE: DNA
<213> ORGANISM: Artificial sequence
<220> FEATURE:
<223> OTHER INFORMATION: Primer

<400> SEQUENCE: 9
gaaaaatttt tt                                                   12

<210> SEQ ID NO 10
<211> LENGTH: 11
<212> TYPE: DNA
<213> ORGANISM: Artificial sequence

```
-continued

<220> FEATURE:
<223> OTHER INFORMATION: Primer

<400> SEQUENCE: 10
aaaaaatttt t                                                              11
```